(12) United States Patent
Leeson et al.

(10) Patent No.: US 11,266,485 B2
(45) Date of Patent: Mar. 8, 2022

(54) METHOD OF MAKING DENTAL RESTORATIONS FROM SINTERED PREFORMS

(71) Applicant: James R. Glidewell Dental Ceramics, Inc., Newport Beach, CA (US)

(72) Inventors: David Leeson, North Tustin, CA (US); Marco A. Jokada, Diamond Bar, CA (US); Vaheh Golestanian Nemargrdi, Orange, CA (US); Hossein Madanipour, Mission Viejo, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 343 days.

(21) Appl. No.: 16/426,180

(22) Filed: May 30, 2019

(65) Prior Publication Data

US 2019/0274796 A1 Sep. 12, 2019

Related U.S. Application Data

(63) Continuation of application No. 16/291,276, filed on Mar. 4, 2019, now Pat. No. 10,973,616, which is a
(Continued)

(51) Int. Cl.
*G06F 19/00* (2018.01)
*A61C 13/00* (2006.01)
(Continued)

(52) U.S. Cl.
CPC ...... *A61C 13/0004* (2013.01); *A61C 13/0006* (2013.01); *A61C 13/0022* (2013.01);
(Continued)

(58) Field of Classification Search
CPC ............ A61C 13/0004; A61C 13/0006; A61C 13/0022; A61C 13/083; A61C 13/20; A61K 6/40; G05B 19/4099; G05B 2219/35134
See application file for complete search history.

(56) References Cited

U.S. PATENT DOCUMENTS

| 5,257,178 A | 10/1993 | Hatfield et al. |
| 5,485,305 A | 1/1996 | Johnson |

(Continued)

FOREIGN PATENT DOCUMENTS

| EP | 2298228 A1 | 3/2011 |
| WO | 09913796 A1 | 3/1999 |

(Continued)

OTHER PUBLICATIONS

Helvey, Gregg A., Zirconia and Computer-aided Design/Computer-aided Manufacturing (CAD/CAM) Denistry, Inside Dentistry, Apr. 2008, vol. 4, Issue 4, Aegis Communications, Newton PA, USA.

*Primary Examiner* — Wissam Rashid
(74) *Attorney, Agent, or Firm* — Charles Fowler

(57) ABSTRACT

A method is provided for shaping a custom dental restoration from a preform, wherein the preform comprises a preform body and a preform stem. A method is further disclosed for generating one or more nesting positions for the restoration design within the geometry of the preform body relative to the position of the preform stem. A method is further disclosed for generating machining instructions based on the selected nesting position to optimize machining for chair-side applications.

20 Claims, 15 Drawing Sheets

Related U.S. Application Data continuation of application No. 15/259,550, filed on Sep. 8, 2016, now Pat. No. 10,258,440.

(60) Provisional application No. 62/215,525, filed on Sep. 8, 2015.

(51) Int. Cl.
*A61C 13/083* (2006.01)
*A61C 13/20* (2006.01)
*G05B 19/4099* (2006.01)
*A61K 6/40* (2020.01)

(52) U.S. Cl.
CPC .......... *A61C 13/083* (2013.01); *A61C 13/20* (2013.01); *A61K 6/40* (2020.01); *G05B 19/4099* (2013.01); *G05B 2219/35134* (2013.01)

(56) References Cited

U.S. PATENT DOCUMENTS

| | | |
|---|---|---|
| 6,267,595 B1 | 7/2001 | Grätz |
| 6,663,390 B2 | 12/2003 | Riley et al. |
| 8,197,299 B2 | 6/2012 | Heinz et al. |
| 8,298,329 B2 | 10/2012 | Knapp et al. |
| 8,551,622 B2 | 10/2013 | Ganley et al. |
| 2002/0119303 A1* | 8/2002 | Pender .................... C04B 41/81 428/325 |
| 2003/0073394 A1 | 4/2003 | Reidt et al. |
| 2005/0008887 A1* | 1/2005 | Haymann ................. A61C 5/77 428/542.8 |
| 2005/0261795 A1* | 11/2005 | Ghosh ................ A61C 13/0004 700/118 |
| 2006/0204932 A1 | 9/2006 | Haymann et al. |
| 2009/0115084 A1 | 5/2009 | Moon |
| 2012/0219930 A1* | 8/2012 | Heinz ................ A61C 13/0022 433/215 |
| 2013/0231239 A1 | 9/2013 | Carden et al. |
| 2013/0288026 A1 | 10/2013 | Johnson |
| 2013/0313738 A1 | 11/2013 | Carden |
| 2013/0316305 A1 | 11/2013 | Carden et al. |
| 2013/0316306 A1* | 11/2013 | Carden ............. A61C 13/0022 433/203.1 |
| 2013/0345853 A1 | 12/2013 | Berman et al. |
| 2014/0308623 A1 | 10/2014 | Chang |
| 2015/0097305 A1 | 4/2015 | Hufschmied |
| 2015/0125821 A1 | 5/2015 | Theelke et al. |
| 2017/0035537 A1 | 2/2017 | Leeson et al. |

FOREIGN PATENT DOCUMENTS

| | | |
|---|---|---|
| WO | 02076328 A1 | 10/2002 |
| WO | 13164411 A1 | 11/2013 |
| WO | 14039268 A1 | 3/2014 |

* cited by examiner

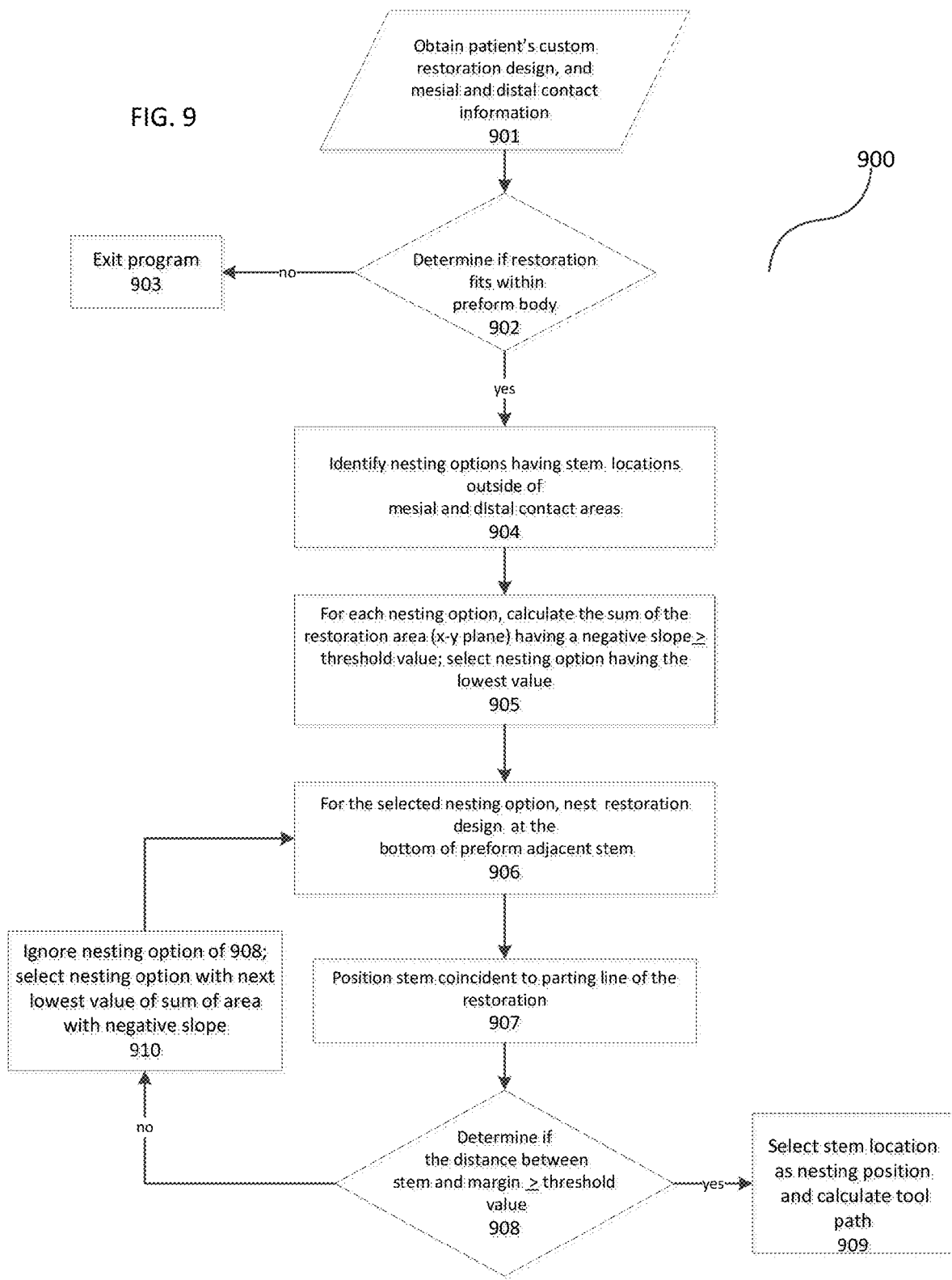

METHOD OF MAKING DENTAL RESTORATIONS FROM SINTERED PREFORMS

RELATED APPLICATIONS

This application is a continuation of, and claims the benefit of and priority to, U.S. patent application Ser. No. 16/291,276, filed Mar. 4, 2019, which is a continuation of U.S. patent application Ser. No. 15/259,550, filed Sep. 8, 2016, now issued as U.S. Pat. No. 10,258,440, which, in turn, claims the benefit of, and priority to, U.S. Provisional Patent Application No. 62/215,525, filed Sep. 8, 2015, all of which applications are incorporated herein, by reference, in their entireties.

BACKGROUND OF THE INVENTION

Ceramic materials known for use in the field of dentistry provide high strength restorations such as crowns, bridges, and the like. Some ceramic materials have flexural strength values exceeding 800 MPa when fully sintered, resulting in restorations that are resistant to chipping, breakage and wear. Material advances provide enhanced aesthetics in color and translucency while maintaining acceptable strength, and restorations may be manufactured from these materials in a cost effective manner.

Dental restorations created by computer assisted design processes may be milled by CAM processes from porous ceramic materials in the green or bisque ceramic stage, using an enlargement factor to accommodate reduction in overall size upon heating to full density. After milling, the porous restoration design is sintered to full density to produce a final restoration. Disadvantageously, the separate steps of milling the porous ceramic dental design and sintering the milled shape to form the final dental restoration, may preclude dentists from making chair-side ceramic restorations, increasing the amount of time a patient must wait for repair.

To reduce the amount of material waste to make a restoration, US2006/0204932 discloses an assemblage or library of "smart" mill blanks pre-configured into geometries and sizes that closely resemble the final dental parts. Material waste may be reduced compared to traditional mill blanks that have a single size and shape, which is desirable when using precious or semi-precious materials. The smart mill blank library is described as comprising a series of blanks with geometries that differ other than by scale, and preferably having at most, one symmetric plane. The blank is mounted in a shaping apparatus by a milling holder that has an orientation-specific attachment key for the milling machine.

Methods of making ceramic restorations from near net shape millable blanks are also known, for example, from commonly owned U.S. Patent Pub. No. 2013/0316305, which is hereby incorporated by reference in its entirety. In this document, a kit is disclosed containing millable blanks of various shapes, each shape designed to closely replicate a restoration shape thus minimizing material removal in chair-side processes. The kit comprises a variety of shapes and shades of restoration blanks, as well as chair-side software, and a chair-side milling machine to convert millable blanks into finished, contoured restorations by a dentist.

SUMMARY OF THE INVENTION

A method for making a custom dental restoration, such as a crown, from a machinable preform is disclosed. The methods are suitable for shaping materials that have sufficient strength and hardness properties into dental restorations that may be directly inserted into the mouth of a patient without the need for a further processing step to strengthen the material after it has been shaped. Methods and apparatus described herein reduce the time required to prepare a finished dental restoration. Advantageously, fully sintered materials known for strength and durability, such as sintered zirconia, may be shaped directly into restorations in chair-side applications or in a laboratory without requiring post-shaping sintering processes. A novel sintered, shaped preform and shaping tool are described, as well as unique nesting methods, machining strategies, and tool paths.

A sintered preform from which a final, custom dental restoration is shaped comprises a body of sintered material and a stem projecting from the center of the preform body. When used in a dentist office chair-side milling machine, the time to create a custom finished product is significantly reduced. Unique features of the sintered preform include the size and shape of the preform body which accommodate most custom restoration designs, and reduce the amount of sintered material to be removed during the process of shaping a dental restoration. Advantageously, the shape of the preform accommodates multiple options for nesting the dental restoration, and methods described herein for selecting nesting positions based on stem placement options enable the generation of unique tool paths for shaping dental restorations from sintered materials.

A method for making the sintered preform is also disclosed that comprises the steps of obtaining unsintered material, shaping the unsintered material into an unsintered, intermediate shaped form having a body and a stem, and sintering the intermediate shaped form to full density to form the sintered preform. Unsintered material may be obtained in the form of a block and then milled into a unitary shaped form that comprises the body (201), stem (202) and optionally, an attachment (203), that is enlarged where necessary to accommodate shrinkage upon sintering. Alternatively, unsintered material may be molded into the unsintered intermediate shaped form, for example, by injection molding. In a further alternative, unsintered material may be first molded into a first shaped form, and then, subsequently milled for shape refinement into a second shaped form prior to sintering.

A method for making a custom dental restoration comprises designing a custom restoration by a known CAD (computer-aided design) process, nesting a CAD dental restoration design within a computer model of a preform body, generating tool paths from a machining strategy and the positional information of the nested restoration design, and machining the sintered preform into the final restoration. In one embodiment, a method comprises nesting the restoration design within the preform body, wherein the preform stem is positioned outside of the proximal contact areas of adjacent teeth. A method further comprises generating at least two tool paths for shaping the occlusal side of the restoration or inner surface of a restoration, wherein a first tool path has a tool path entry point adjacent the preform stem, and a second other tool path has a tool entry point on the front side of the preform—the side that is opposite the stem. In another embodiment, at least two tool paths are provided for shaping the restoration from the occlusal side and at least two additional tool paths are provided for shaping the inner surface side of the restoration.

BRIEF DESCRIPTION OF THE DRAWINGS

FIG. 9. A flowchart of a method for nesting a restoration design in a preform according to one embodiment.

DETAILED DESCRIPTION

A method for making a custom dental restoration is described herein. A dental restoration machined from a machinable preform is illustrated in FIG. 1A (100). In one embodiment, the preform comprises a sintered preform material that may be machined chair-side in a dentist's office into a final dental restoration, such as a crown, and secured directly into the mouth of a patient without requiring post-process sintering. A method is provided for machining the sintered preform into a custom final dental restoration that reduces the time required to prepare a fully sintered final dental restoration. The methods and apparatus disclosed herein comprise novel features including a unique preform design, nesting strategies, tool paths and machining strategies. In a further embodiment, a kit is provided that comprises a preform, a grinding tool, and computer programs or modules for nesting a restoration design within the preform and generating tool to shape a final restoration chair-side, without the need for sintering after shaping the restoration.

Figure 2B:
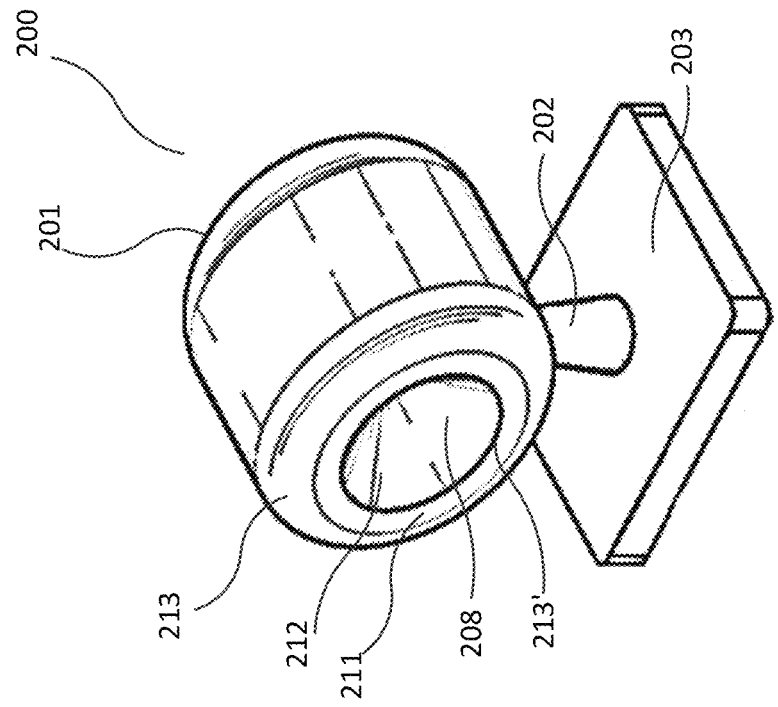
FIG. 2B. A bottom perspective view of a graphic representation of a preform according to one embodiment.
Figure 2A:
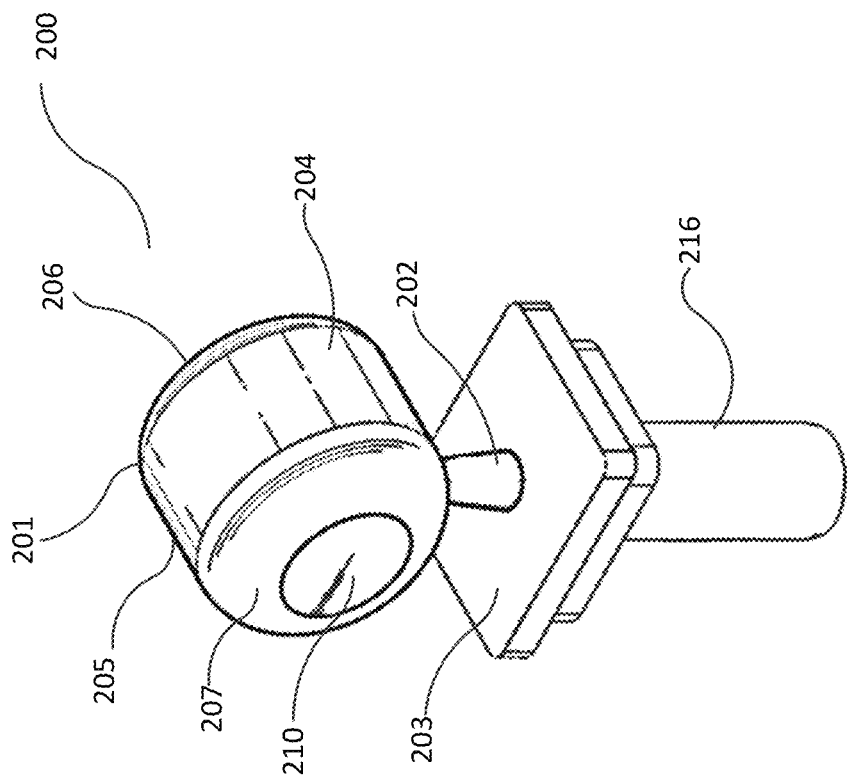
FIG. 2A. A top perspective view of a graphic representation of a preform on a mandrel according to one embodiment.

Illustrated in FIGS. 2A and 2B, one embodiment of a preform (200) comprises a body (201) from which a dental restoration (101) is machined, and a stem (202) that projects from the body (201). As illustrated in FIG. 2A, the sintered preform (200) may comprise an attachment (203) that is attached to a mandrel (216), for securing the preform (200) to a shaping machine. Machines suitable for use herein have at least 3 axes, such as a 3+1 axis CNC machine. After machining, the restoration (101) is complete, the remaining stem (102) of the sintered preform may be easily removed for immediate placement on a patient's tooth preparation.

Figure 2C:
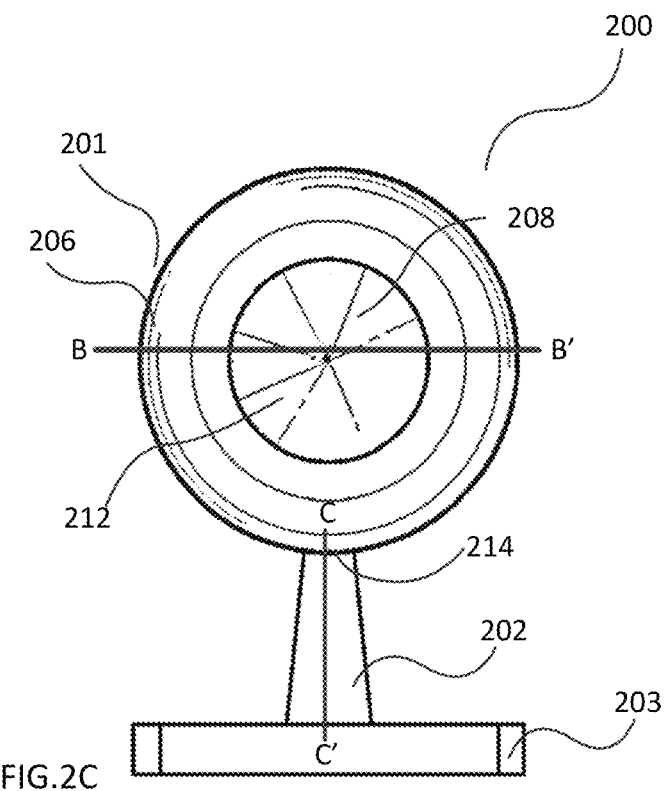
FIG. 2C. A bottom view of a graphic representation of a preform according to one embodiment.

In one embodiment, a sintered preform (200), illustrated in FIGS. 2A, 2B, 2C, and 2D, has a circular-cylindrical body (201) having a curved outer surface (204) and a cylinder length (line A-A') that is in the z-axis direction of a shaping tool of a CNC machine. A center portion (205) of the body (201) extends between bottom end region (206) and a top end region (207). In FIGS. 2A, 2B, 2C, and 2D, the length (A-A') of the cylindrical body (201) is substantially orthogonal to the length (along line C-C') of the stem (202) in the y-axis direction. In this embodiment, the stem projects from a stem contact point on the outer, curved surface (204) of the center portion (205) of the cylindrical body, and extends to an attaching member (203) for direct or indirect attachment to a shaping machine. The sintered preform of FIGS. 2A-2D further comprises a cavity (208). The curved outer surface (204) of the center portion of the cylindrical body exemplified in FIGS. 2A-2C is substantially smooth.

In the embodiment illustrated in FIG. 2C, the cylindrical body (201) comprises a substantially circular cross-section (line B-B') parallel to the bottom and top end surfaces (209 and 210). The ends of the cylindrical body comprise circular bottom and top end surfaces (209 and 210, respectively). In this embodiment, the bottom end surface (209) has a concavity (211) from which a cavity (208) extends inwardly into the cylindrical body and defines a preform inner surface (212). The outer diameter of a circular cross-section of the center portion from which the restoration design is shaped may be from about 12 mm to about 20 mm, or from about 13 mm to about 18 mm, or from about 14 mm to about 17 mm. The length of the preform body between the top end and the bottom end is sufficient to accommodate the height of most dental restoration designs when measured, for example, from the highest point of the occlusal surface to the lowest point on a tooth margin; thus, the length of the preform body or the center portion of the preform body may be less than 20 mm, or less than 18 mm, or less than 16 mm, or less than 15 mm, or may be between about 10 mm and 15 mm. In some embodiments, the ratio of the cross-sectional diameter of the center portion to the length of the preform body is greater than 1.0:1.0.

The preform body (201) may comprise a shape other than a cylinder, for example, an ellipsoid cylinder, a polyhedron, curved polyhedron, a cylinder with flattened surfaces, a square, a square with rounded edges, and the like. In one embodiment, the dimensions of a preform body having an irregular shape provide for a full rotation of the restoration design around the z-axis. A preform body may have a cross-sectional geometry (parallel with top and bottom surfaces) with an inscribed circle diameter greater than approximately 12 mm and a circumscribed circle diameter less than approximately 20 mm at the stem contact point.

In some embodiments, the body (201) may have a substantially uniform cross-sectional dimension throughout the body length, wherein the top end surface (210) and/or bottom end surface (209) are flat. Alternatively, the preform may comprise a shaped edge (213) between the curved outer surface (204) of the preform body (201) and top end surface (210) and/or bottom end surface (209), defining the top and bottom end regions (207 and 206, respectively). The preform body may also, or alternatively, have a shaped edge (213') around the cavity (208) perimeter. For example, as illustrated in FIGS. 2A-2D, a filleted edge surrounds the bottom end surface concavity (211).

In some embodiments, the preform comprises at least one chamfered edge, at least one filleted edge, or both a chamfered edge and filleted edge. For example, as illustrated in FIGS. 2A-2D, a filleted edge surrounds the bottom end surface concavity (211). In other embodiments, the shaped edge (213) between the cylindrical curved outer surface (204) and bottom or top end surfaces (209, 210) may be chamfered. The shaped edge (213') around the cavity (208) perimeter may be chamfered. The bottom and/or top end regions (206 and/or 207) of the preform body may have a cross-sectional width or diameter that is smaller than the width or diameter of the center portion (205). In some embodiments, a preform having a shaped edge has less sintered material to be removed when making the final restoration crown shortening the shaping time. The shaped edge may also facilitate access to the cavity by a shaping tool.

The stem (202) supports the sintered preform body (201) in the shaping machine while shaping the body into a final dental restoration. The stem (202) bridges the cylindrical body (201) and optional attaching member (203), and the stem length axis is orthogonal to the length of the cylindrical body (A-A'). In some embodiments, the stem length axis is within about 30 degrees or within about 45 degrees of orthogonal, relative to the body. In one example, the first stem end extends from the center portion of a cylindrical body, and in a further embodiment, the stem contact point is approximately equidistant between the bottom end (209) and the top end (210) of the preform body.

In some embodiments, prior to shaping the sintered preform, a stem length (along line C-C') may be greater than the width of the stem at the first stem end (214) proximate the cylindrical body. (For purposes herein, width may be used interchangeably with diameter, for example, in embodiments in which the stem has a circular cross-section). The stem length may be between about 3 mm and about 12 mm, or between about 3 mm and about 10 mm. In some embodiments, the stem length may be greater than about 3 mm, or greater than about 4 mm, or greater than about 5 mm, or greater than about 6 mm, or greater than about 8 mm. In one embodiment, the width (diameter) of the first stem end (214) is less than the width (diameter) of the second stem end (215) proximate the attaching member (203). The width (diameter) of the first stem end may be about 1 mm to about to about 4 mm, or from 1 mm to about 3 mm, or about 1.5 mm to about 3 mm, or 1.5 to about 2.5, or less than about 4 mm, or less than about 3 mm, or less than about 2.5 mm. In some embodiments, the ratio of stem length to the first stem end (214) width or diameter (proximate the preform body) is greater than about 1.5:1, or greater than about 2:1, or greater than about 3:1.

In one embodiment, the stem length is greater than the diameter of the shaping tool. In this embodiment, the stem length forms a space between the preform body (201) and an attachment (203) for entry of a shaping tool near the first stem end for entry to a first tool path without the tool tip contacting the sintered preform material, and thereby reducing tool wear. The flex strength of the stem (202) at the first stem end (214) is sufficiently high to support the sintered preform (200) during machining from a sintered state, and sufficiently low for the finished restoration to easily be broken off from the stem, for example, by hand. The stem shape may be a cylinder, tapered cylinder, cone, prism or the like, and is connected to the center portion of the preform body at the stem contact point by a first stem end.

Figure 2D:
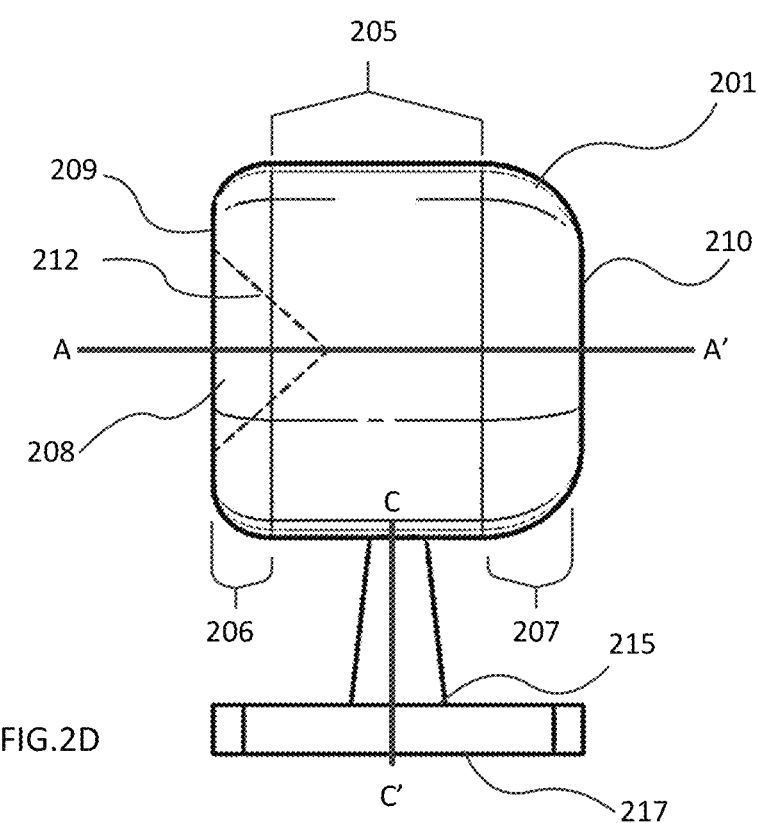
FIG. 2D. A side view of a graphic representation of a preform according to one embodiment.

As exemplified in FIGS. 2B-2D, a preform cavity (208) begins at an end surface (210, 209) of a bottom or top end region (206 or 207) and extends into the body (201). The contour of the cavity forms a preform inner surface (212) that is accessible by a shaping tool. The shape of each cavity may be the same or different, and may comprise, but is not limited to, an inverted cone, dome, cylinder, trough, or the like, or may have an irregular shape. An opening or breakout geometry of the cavity may have a width (or diameter, for example where the breakout area is circular) that is between about 20% and 80% of the outer diameter or width of the center portion of the preform body. The cavity opening or break-out dimension may have a surface area that is about 50% to about 80% of the surface area of a top end face, a bottom end face, or a center portion cross-section. The approximate cavity depth may be between 5% and 50% of the length of the preform body. A circular cavity opening may have an inner diameter of up to about 75 percent of the outer surface diameter of the preform body when measured from the end face.

The sintered preform may be attached directly or indirectly to a shaping machine by an attaching member (203) that is joined to the second end of the stem (215). FIG. 2A illustrates an embodiment in which the attaching member (203) is connected to a mandrel (216) for indirect attachment of the preform to a shaping machine. The attaching member (203) may have a substantially flat surface (217) shaped as a rectangle, circle, or square, as exemplified in FIG. 2A, or, for adhesive attachment to a mandrel.

Figure 3:
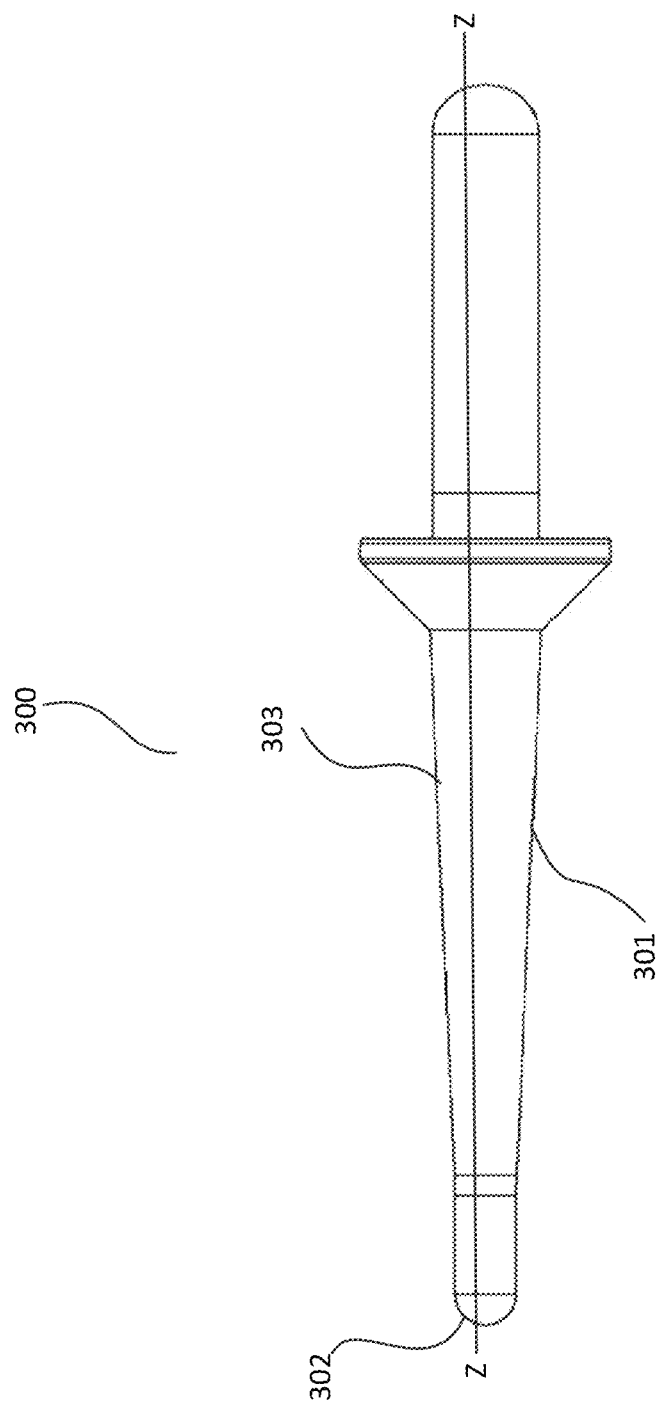
FIG. 3. A side view of a graphic representation of a grinding tool according to one embodiment.

In further embodiments, methods are provided for machining a dental restoration from a sintered preform from CAD/CAM-based systems. Data regarding anatomical information about the patient's tooth preparation, and optionally, surrounding teeth and original tooth structure, are collected and stored in a computer or computer storage media. A computer model of a desired restoration design (107) may be created manually by an operator, or automatically proposed, in a dental restoration CAD system. Known design systems, such as IOS FASTDESIGN™ System (10S Technologies, San Diego, Calif.), are suitable for designing dental restorations for use herein. The computer model of a patient's dental restoration design may be selectively nested within a computer model of the preform (108) to establish optimal machining conditions for a selected CNC machine and shaping tool, such as a milling or grinding tool. A suitable chair-side milling machine includes, but is not limited to the TS150™ chair-side milling system (IOS Technologies, San Diego, Calif.), and an exemplary grinding tool (300) suitable for use herein is illustrated in FIG. 3. Positional data of the nested restoration design (for example, FIGS. 6A, 6B, 7A and 7B) may be provided to the CAM system to calculate tool paths from machining strategies (FIGS. 4A, 4B, 5A and 5B) including lace direction, XY step over, maximum Z increments, feed rates, coolant parameters, and the like, based on the milling machine selected and properties of the grinding tool, as further described herein.

A computer-implemented method for nesting a restoration design within the geometry of a preform is provided. In one embodiment, dental CAD software is used to generate a computerized 3D model of the restoration design (107). The 3D model of the dental restoration design and a computer model of a preform (108) are aligned generally along z-axes within a CAD system. A restoration design may be nested within the geometry of a preform so that the cavity on the inner surface (105) of the restoration design (e.g., the inner surface of the dental restoration that is designed to contact and attach to a tooth preparation), is aligned to be adjacent the cavity (109) of the preform. By aligning the restoration's concave inner surface (105) adjacent the cavity of the preform, the amount of material removal during the shaping process is reduced.

In one embodiment, the step of nesting includes rotation around the z-axis, and translation in the z-, x- and y-axes, orienting the position of the preform stem relative to the computer model of the restoration design. The position of the stem relative to the outer surface of the restoration design may be selected that optimizes machining conditions and material removal. In one embodiment, a restoration design is nested within the geometry of a preform so that the first stem end is located on or near the parting line of the restoration design, between occlusal surface (103) and margin (104), as exemplified in FIGS. 1A and 1C. The restoration design may be nested so that a minimum distance value is established between the first stem end and the restoration tooth margin (104) and/or the proximal contact points. By nesting the restoration design so that the preform stem contact point is at a distance from the margin or mesial and distal contact points of the restoration, variations in the surface geometry of the final dental restoration that may result upon removal of the stem may be minimized in these areas thereby increasing the likelihood that optimal fitment is achieved in the final restoration.

Figure 6A:
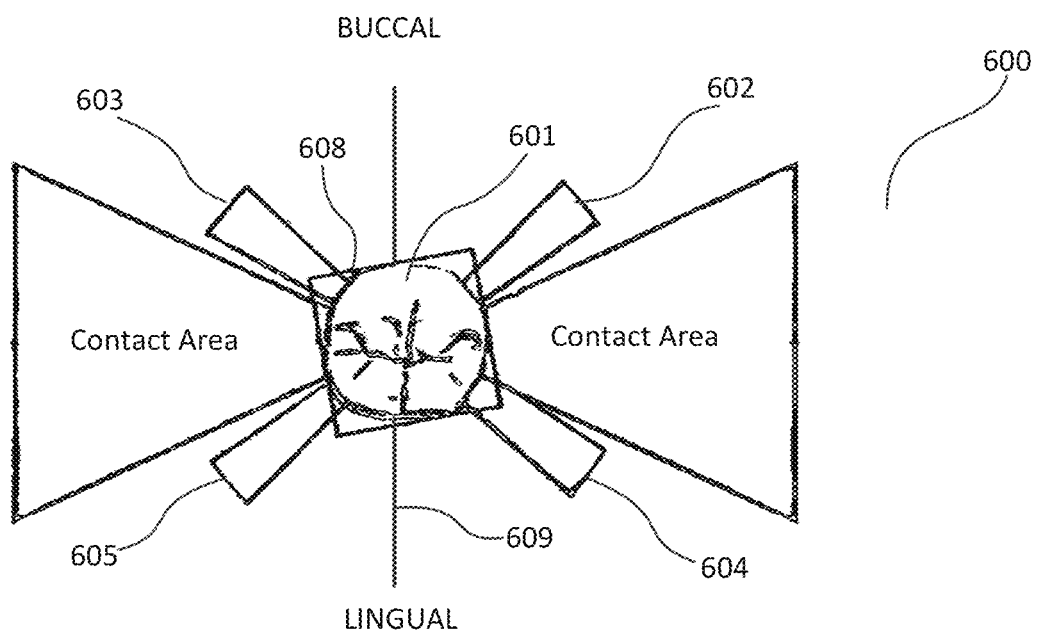
FIG. 6A. A graphic representation of a nesting method showing contact areas according to one embodiment.
Figure 6B:
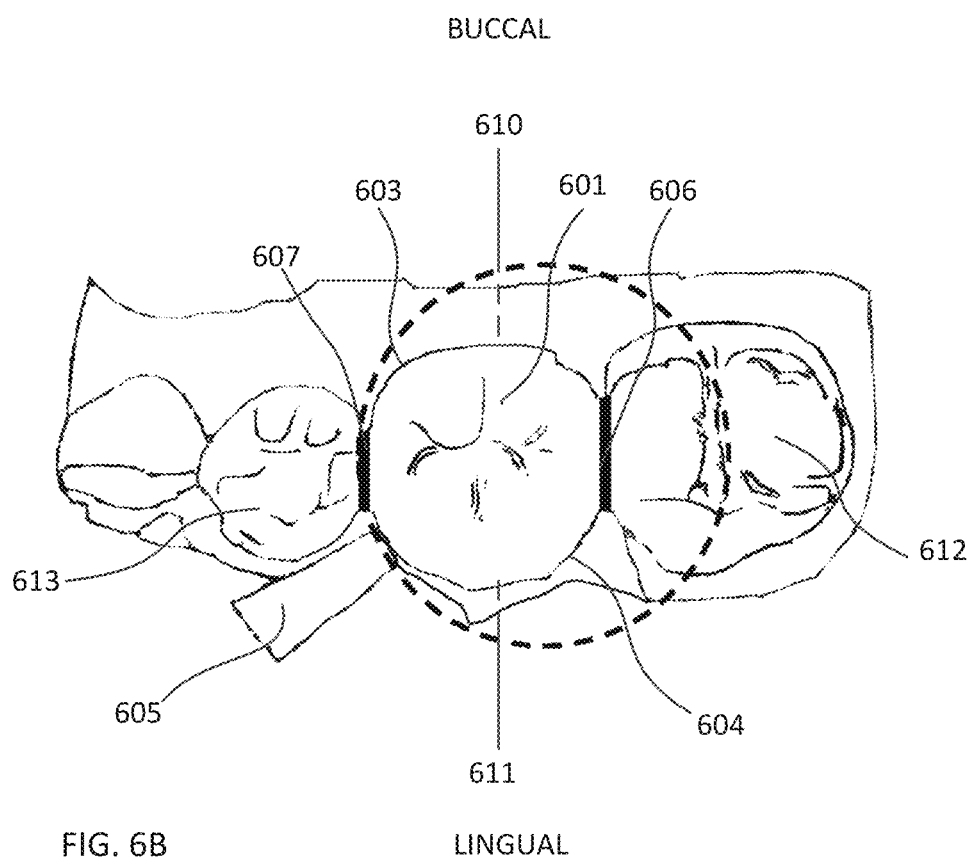
FIG. 6B. A graphic representation of a nesting method showing contact areas between adjacent teeth of a preparation from an occlusal view.

FIGS. 6A and 6B illustrate a method (600) for nesting the restoration design (601) within the preform geometry comprising arranging computer models of the restoration design and preform at a rotation around the z-axis, and positioning the length of the stem (along the y-axis (C-C')) and stem contact point outside of the proximate contact areas (606 and/or 607) of neighboring teeth. A proximal contact area (606 or 607) refers to the tooth surface that may touch an adjacent tooth in the same arch (FIG. 6B) when the final restoration tooth (601) is placed on the patient's tooth preparation. A distal proximal contact area (606) includes the distal surface area of the restoration tooth that may contact the mesial surface a more posteriorly positioned adjacent tooth (612); the mesial proximal contact area (607) encompasses the mesial surface of the restoration tooth that may contact the distal surface of an anteriorly oriented adjacent tooth (613). Distal and mesial proximal contact areas (606 and 607) may be identified by a technician, or automatically identified by the restoration design software. By nesting the restoration design within the preform so that the stem contact point is outside of the mesial and/or distal contact areas (606, 607), the stem will not be coincident to a mesial or distal contact point in the final restoration.

The preform stem may be optionally positioned on the buccal surface (610) or on the lingual surface (611) of the restoration design (601), outside of the proximal contact areas (606 and 607). In a further embodiment, the model is rotated for alignment of the axis of the stem length (C-C') between a buccal-lingual plane and a mesial-distal plane of the restoration design. A restoration design may be nested within a model of the preform body to achieve a mesio-buccal stem placement position (603), between the buccal surface and the proximal mesial contact area, or alternatively, a mesio-lingual stem position (605) between the lingual surface and the mesial proximal contact area of the design. In further alternative embodiments, a disto-buccal stem position (602) may be established by orienting the stem between the distal contact area and the buccal surface, or a disto-lingual stem position (604) between the distal contact area and the lingual surface, respectively.

The restoration design may also be translated along one or more of x-, y- and z-axes, when nesting within the geometry of the preform model. For example, translation along the z-axis adjusts the distance between the occlusal surface (103) of a restoration design and top end (210) of the preform model, or the distance between the margin (104) of a restoration design and bottom end (209) of the preform. Translation of the restoration design along the z-axis may be performed to locate the first stem end at a distance between the occlusal surface (103) and margin (104), away from the margin of the restoration design. Moreover, the restoration design may be translated along the z-axis, y-axis or x-axis to align the cavity (105) of a restoration design adjacent a preform cavity (208) to facilitate access of the machine tool (300) directly into the preform cavity to shape the restoration design's inner surface. The restoration design may be translated along the y-axis or x-axis to change the restoration design's position relative to the outer surface of the preform body. For example, the restoration design may be positioned directly adjacent the first stem end minimizing the amount of material (106) to be removed from the dental restoration outer surface after shaping. In an embodiment, threshold parameters may be established that provide for a minimum distance between the outer surface of the preform body and the outer surface of the restoration design.

Figure 4A:
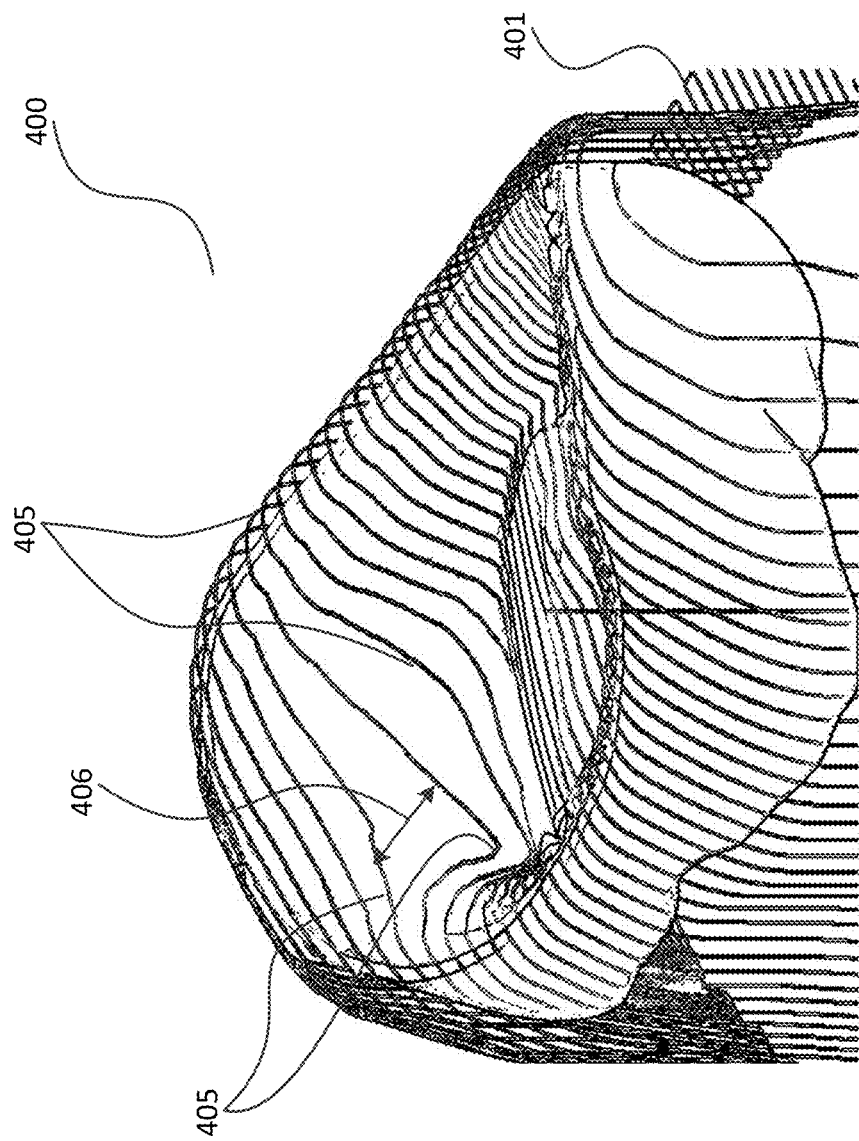
FIG. 4A. A graphic representation of a tool path applied to a restoration design.
Figure 4B:
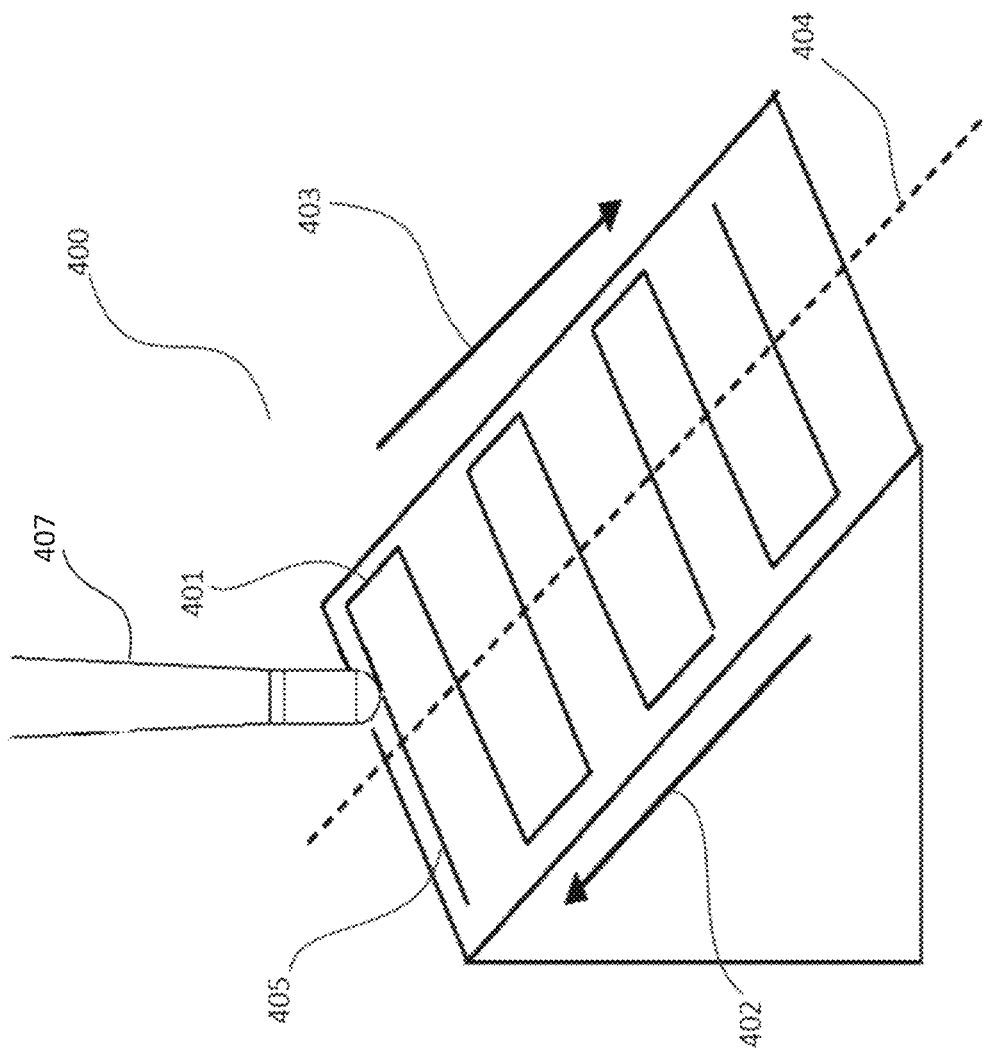
FIG. 4B. A graphic representation of a portion of a tool path on a slope according to one embodiment.

Positional data of the nested restoration design may be provided to the CAM system to calculate tool paths to shape the final restoration from the preform. A method is provided comprising obtaining a machining strategy that comprises two or more machining steps to shape a restoration from the nested design. Each machining step may comprise a tool path for machining a portion of the restoration including machining strategy elements such as lace direction, XY step over value, maximum Z increments, feed rates, coolant parameters, and the like. In one embodiment, a tool path is provided overlaying a restoration design that follows a lacing, or zig-zag, pattern (400) as illustrated in FIGS. 4A and 4B. The parallel lacing pattern comprises generally straight sequential tool path lines (405) separated by a distance (401). Tool paths may be established using linear interpolation methods based on XYZ machining positions, and appropriate spacing between tool path lines (405) or passes, to optimize machining conditions. The planar spacing between lines of the lacing pattern, or step-over distance (401), may be an arbitrary increment, for example, based on tool dimensions (407). Alternatively, the step-over distance (401) in the Y-direction between sequential lines (405) of the tool path may be independently adjusted to insert additional tool path lines (405). For example, if the distance (406) between two tool path lines (405') exceeds a threshold value in the Z direction (e.g., a maximum Z increment value in a Z-negative direction) in one area of the tool path sequence, the step-over distance (401) between adjacent lines may be decreased and additional tool path lines may be inserted in that area to decrease the Z increment distance between two tool path lines until the threshold value is met or not exceeded.

Figure 5B:
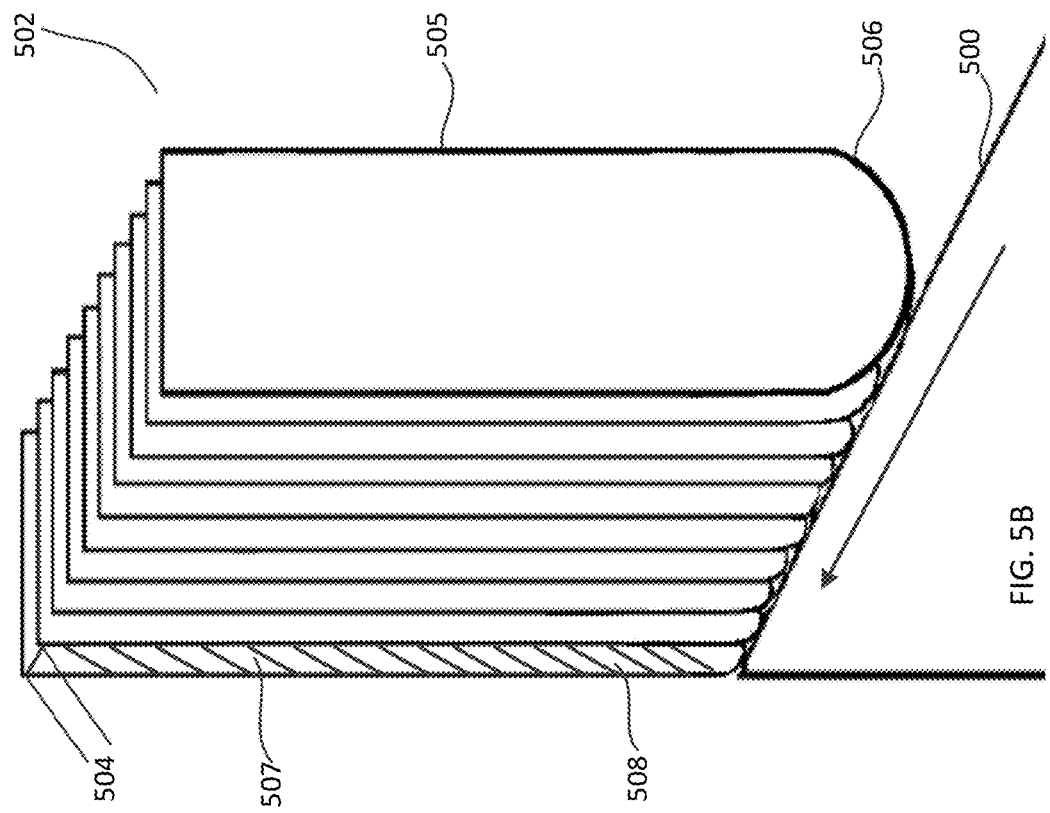
FIG. 5B. A graphic representation of an up-hill tool path according to one embodiment.
Figure 5A:
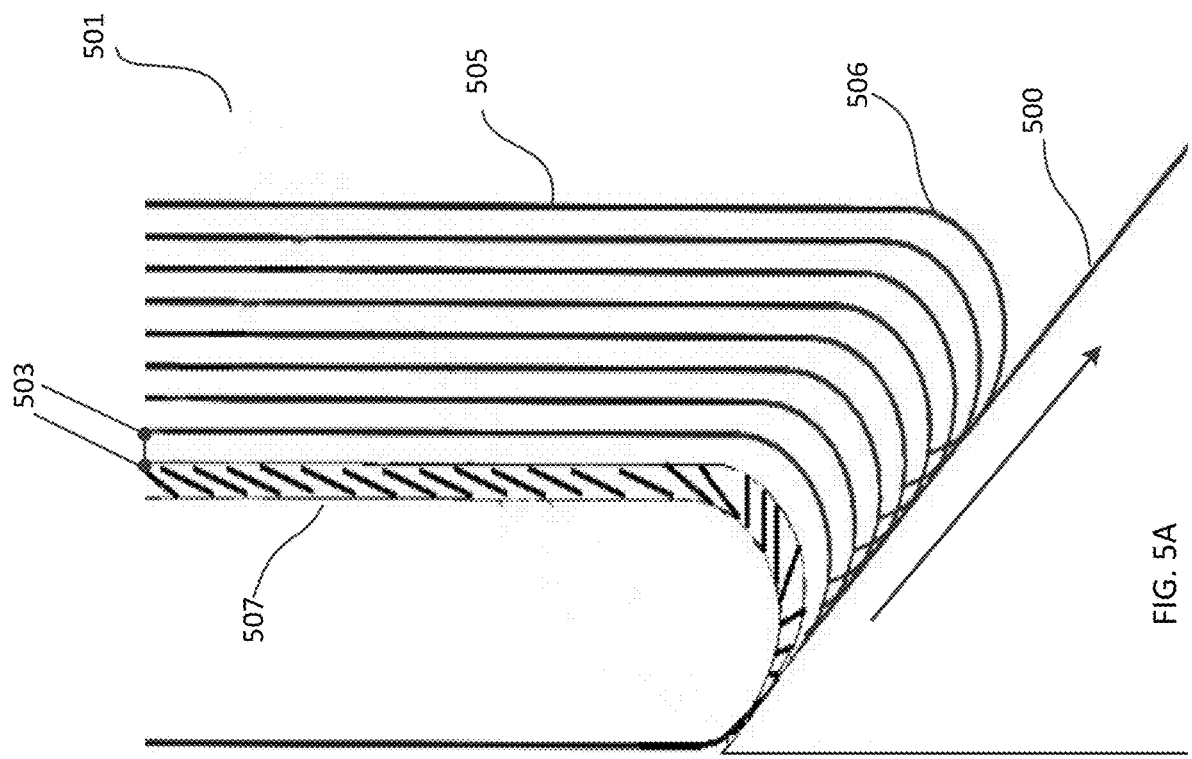
FIG. 5A. A graphic representation of a down-hill tool path according to one embodiment.

FIGS. 5A and 5B depict cross-sectional representations of FIG. 4B (404), and the movement of a tool (e.g., 300 407, 505) across a slope (500). The Z-axis of the grinding tool (300) moves toward Z-positive (402), for example, as the tool is lifted away from the surface to be machined, and projections through the tool path may occur towards Z-negative (403). Where the step-over (503) position of the tool (505) is toward Z-negative, a 'down-hill' (FIG. 5A) grinding path (501) results. At least a portion of the material removal (507) in a down-hill movement occurs by the tool tip (302, 506). Material removal by the tool tip may result in heating of the tool (300), wear on the tool tip (302), and excessive wear on the grinding media (303), such as diamonds embedded in an alloy coating on the tool shank (301). Where the step-over (504) position is inclined toward Z-positive (FIG. 5B), an 'up-hill' (502) grinding path provides material removal (507) by a tool side surface (508) reducing material removal by a tool tip (506), thereby reducing wear on the tool. A method is provided comprising machining strategies that are optimized for material removal in up-hill movements. However, where z-negative milling is unavoidable, a method is provided that limits the amount of continuous machining that occurs in the (down-hill) z-negative direction, for example, by minimizing the length of each tool path.

In one embodiment, a method for minimizing the percentage of Z– negative direction movement of a grinding tool comprises implementing a nesting strategy for optimizing the nesting position of a restoration design within the preform geometry, and generating tool paths from the selected nesting position. In one method, stress or wear on a grinding tool is reduced by selecting a nesting position that reduces the length of tool path lines across a dental restoration design. For some dental restorations, the longest dimension of the restoration design is the width between buccal (704) and lingual (705) surfaces (represented by e.g., line 703), and/or the width between mesial (706) and distal (707) surfaces. Machining strategies in which a tool passes either parallel to the longest dimension of a tooth, or orthogonal to the longest dimensions of a tooth, may place stress on the grinding tool. In one embodiment, a method comprises selecting a nesting configuration in which line (703) separating the buccal and lingual sides of the restoration design (700), is not orthogonal to the stem length, so that tool path lines that run orthogonal to the stem length (Y-axis) are not parallel to line (703). In one embodiment, an embodiment of the method is provided for nesting a restoration design (depicted from the inner surface (FIG. 7B, 708) and occlusal surface (FIG. 7A, 709)). The restoration design, rotated around the Z-axis, is positioned so that line (703) separating the buccal and lingual surfaces is off-set from the stem length (y-axis) (701), and line 703 is not parallel with the stem length axis. In another embodiment, the method comprises nesting a restoration design within a preform body so that a line (703) separating the buccal and lingual surfaces is both off-set from the stem length axis (y-axis) and off-set from orthogonal to the stem-length axis, so that the line (703) is neither parallel to nor orthogonal to the stem-length axis.

Figure 7A:
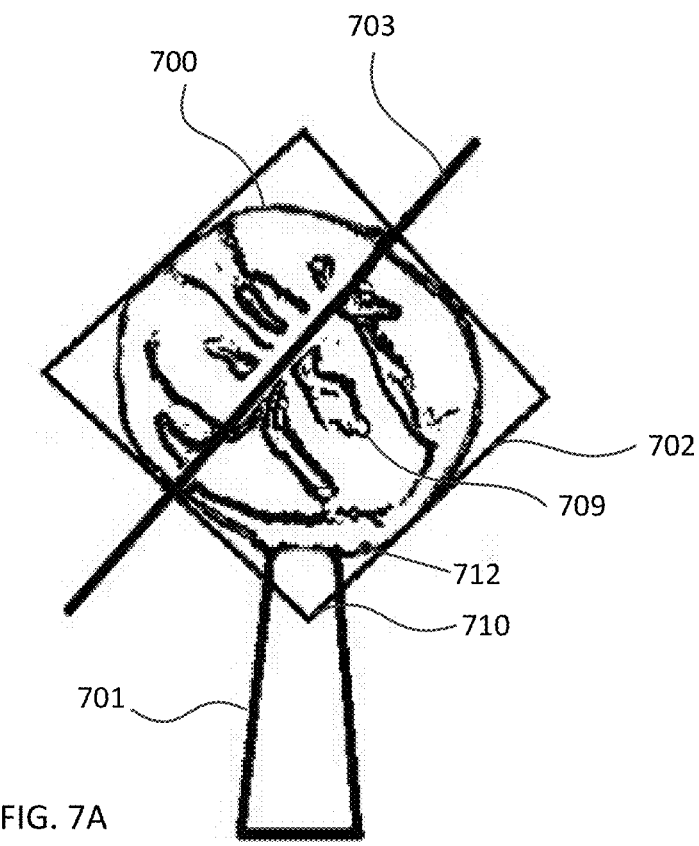
FIG. 7A. A graphic representation of an occlusal view of a restoration design and nesting method according to one embodiment.
Figure 7B:
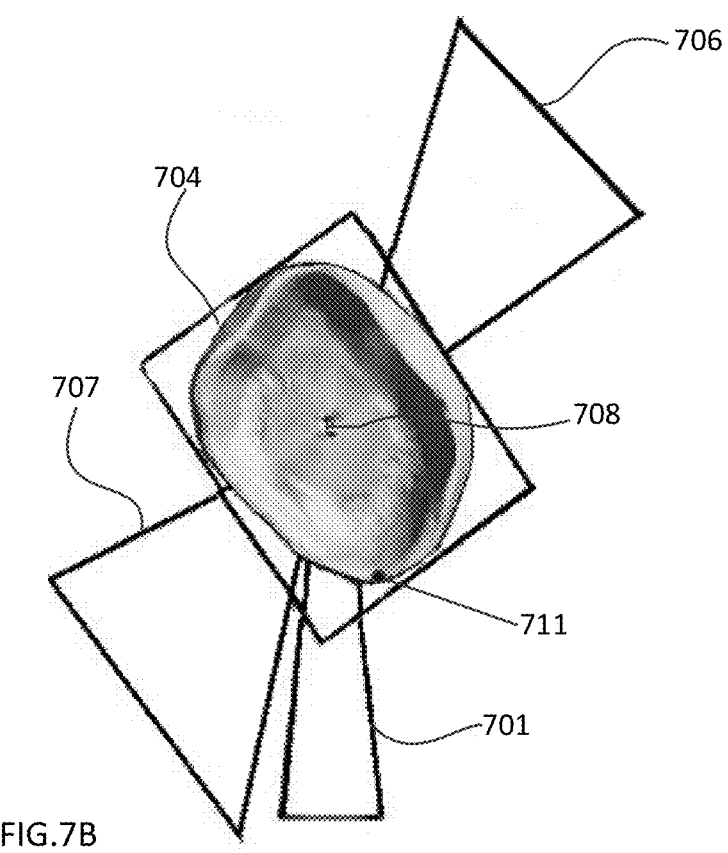
FIG. 7B. A graphic representation of an inner-surface view of a restoration design and nesting method according to one embodiment.

For illustrative purposes, a quadrilateral box (702) is depicted having adjacent buccal, lingual, mesial and distal side surfaces bounding the outer surfaces of restoration design. In this embodiment, the restoration design within the box is angled in a diamond configuration (710) relative to the position of the stem (701), so that the sides are neither orthogonal nor parallel to the stem length. Thus, a method is provided comprising nesting a restoration design in diamond configuration relative to the stem and providing a tool path sequence having tool path lines orthogonal to the stem length (y-axis) (701), and when used, e.g., with a parallel lacing tool path pattern (with XYZ machining positions), the length of the resulting tool paths through the mesial-distal width of the tooth is reduced. In one embodiment, the Y-axis of the stem of the preform design is positioned at an angle between mesial and distal (608) surfaces and buccal and lingual (609) surfaces, resulting in a diamond configuration as seen in FIGS. 7A and 7B, reducing the length of the tool path across a restoration when grinding in a down-hill (Z-negative) position for at least a portion of the grinding sequence.

In one embodiment, a restoration design is nested in a plurality of positions, as described above. In one embodiment, for each nesting position, a negative slope value is calculated for the inner surface or occlusal surface. Negative slope values are calculated as the percentage of a restoration design surface area that is determined to have a negative slope greater than a threshold angle, such as 10°, 15°, 20°, or 30°, or greater, when viewed from the machining direction. Optionally, a negative slope value for a restoration may be the sum of the percentage of surface area having a negative slope greater than a threshold angle for both occlusal and inner surfaces. The surface area with negative slope corresponds to area in which shaping may be performed by down-hill (Z-negative) machining of the tool at an angle greater than or equal to the threshold angle. For example, in one embodiment using an stl. file format, an occlusal or inner surface of a restoration design may be analyzed to determine what percentage of a triangulated surface geometry is sloped greater than a threshold value relative to normal, when viewed from a machining direction. The nesting position in which the restoration design has the lowest negative slope value, corresponding to the percentage of surface area with negative slope greater than or equal to a specified threshold value for inner surface and/or occlusal surfaces, is selected as the nesting position from which to calculate a tool path.

A flowchart comprising a method (900) for nesting a restoration design is provided in FIG. 9. In one embodiment, a method comprises obtaining patient's custom restoration design, and mesial and distal contact information (901), and determining if a restoration fits within the geometry of the preform body (902). In one embodiment, a threshold value may be established so that the distance from the preform outer surface and the restoration design outer surface is greater than a set value, such as greater than 0.2 mm. If the restoration design does not fit within the preform geometry, the program may be exited, and a different restoration option may be pursued by the dentist If the restoration design fits within the preform geometry, nesting options may be identified having a preform stem location that is outside of mesial and distal contact areas (904) of adjacent teeth in the same arch. For each nesting option, the sum of the restoration surface areas (x-y plane) having a negative slope greater than a threshold value is calculated for both the occlusal and inner surfaces, and then summed. A nesting option having the lowest percentage of surface area having a negative slope value (905) that is greater than a threshold value may be selected. For the selected nesting option, the restoration design is nested at the bottom of preform adjacent the stem (906). For the selected nesting option, the stem is positioned coincident to the parting line of the restoration (907), or the line around the position of maximum dimension between the restoration's occlusal surface and margin, for example, when viewed from the occlusal surface. In a further step (908), the distance of the first stem end from the restoration design tooth margin is determined, for example, to determine if the distance between the stem attachment and the restoration margin will be greater than a threshold value (e.g., greater than 2 mm) upon completion of shaping the restoration. If the distance of the stem (at the point of attachment to the dental restoration) from the margin is less than the threshold value, the tooth restoration margin may be damaged upon removal of the stem after shaping, so the nesting option may be ignored or refused (910), and a second nesting option may be selected having the next lowest value for the sum of percentage of surface area with negative slope. Any of the nesting and analysis step processes may be repeated until a final nesting option is selected that meets one or more threshold values, such as the distance of the stem from mesial and distal contact areas, distance of the stem from margin and/or occlusal surface, and/or the percentage of Z-negative direction machining for occlusal and inner restoration design surfaces. After selection of a final nesting position, a tool path sequence (909) is calculated.

Figure 10:
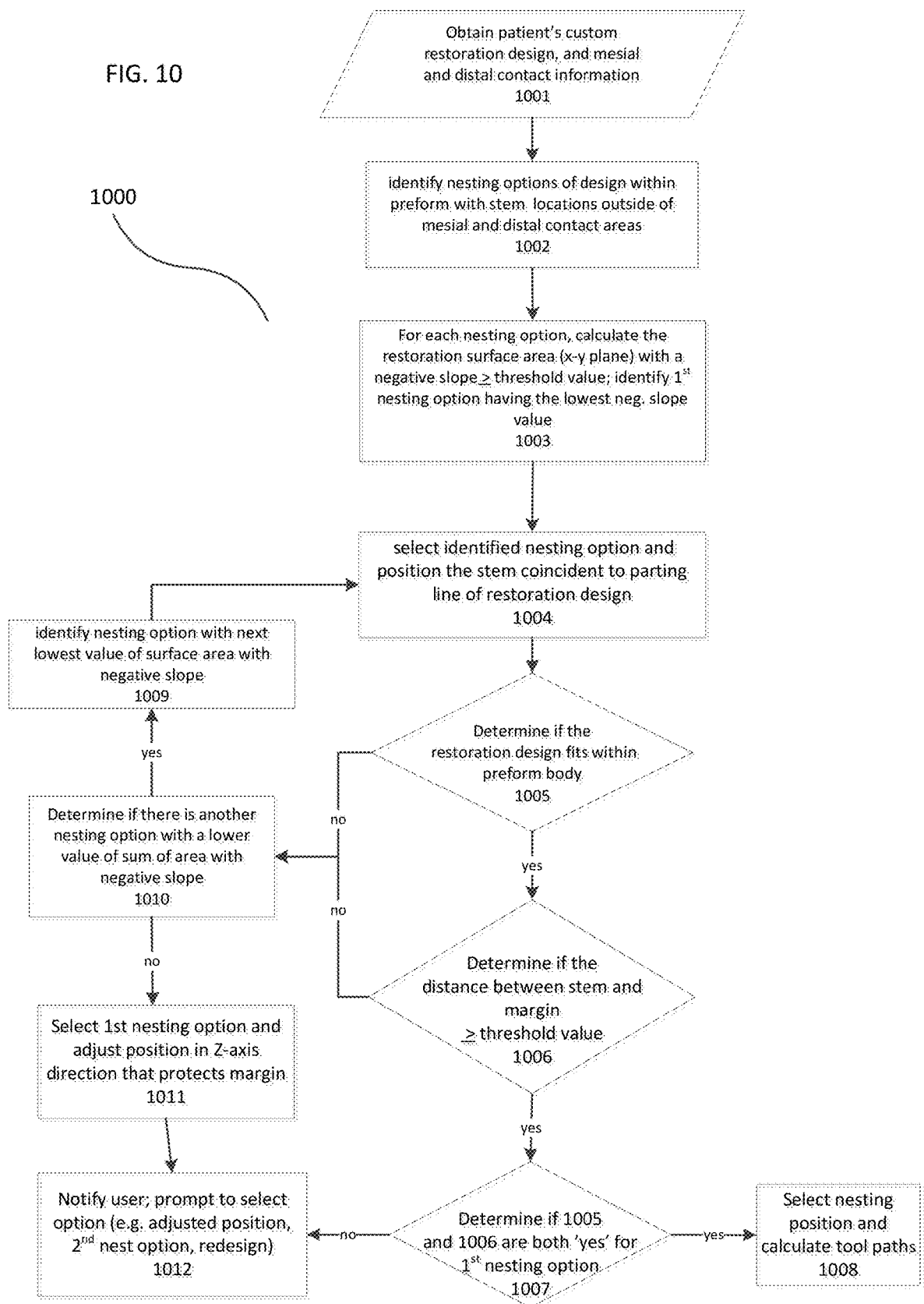
FIG. 10. A flowchart of a method for nesting a restoration design in a preform according to one embodiment.

In a further embodiment exemplified by the flowchart of FIG. 10, another method (1000) for nesting a restoration design is provided. The method comprises obtaining patient's custom restoration design, and mesial and distal contact information (1001), and identifying nesting options for the restoration design within the preform body. Nesting options are identified in which the stem first end does not connect with the restoration design at mesial and/or distal contact points of the restoration design and adjacent teeth. In one embodiment, two nesting options may be provided in which the stem contacts the restoration design on the buccal side of the restoration, for example, distal-buccal or mesial-buccal stem positions. For each nesting option, the percent of the restoration surface areas (x-y plane) having a negative slope greater than a threshold value is calculated for the occlusal and/or inner surfaces, and optionally, the occlusal and inner surface values are summed (1003). A first nesting option having the lowest percentage of surface area with a negative slope (1004) greater than or equal to a threshold value may be identified. The first identified nesting option may be selected, and the position of the restoration design within the preform may be adjusted so that the stem is coincident to the parting line (1004). For the first selected nesting option, it may be determined if the restoration design fits within the preform body (1005), for example, if the distance from the preform outer surface and the restoration design outer surface is greater than a minimum threshold value, such as greater than 0.2 mm. It may also be determined if the distance between the stem and the margin is greater than a threshold distance (1006), e.g., 1 mm. If both parameters of steps (1005) and (1006) are met (1007), the first nesting position may be accepted, and a tool path may be calculated (1008) from the nesting position of the restoration within the preform. If either parameter of (1005) or (1006) is not met, another nesting option having the next lowest percent of surface area with a negative slope may be identified (1010, 1009), and evaluated by the processes of (1004), (1005), and (1006). If a second or subsequent nesting option meets the parameters of (1005) and (1006), the user of the program may be notified that a second or subsequent nesting option meets the parameters, and the user may be prompted for further action, such as to evaluate the nesting option, to select the nesting option, to provide further adjustment to the nesting option, or to select another restoration option. If no nesting options meet the parameters of (1005) and/or (1006), the first nesting option having the lowest surface area may be selected (1011), and adjusted, for example, in the Z-axis direction within the preform to establish the best possible fit of the restoration design within the preform. The user may be notified (1012) that no options met all parameters, and the user may be prompted for further action, as described above.

Figure 8A:
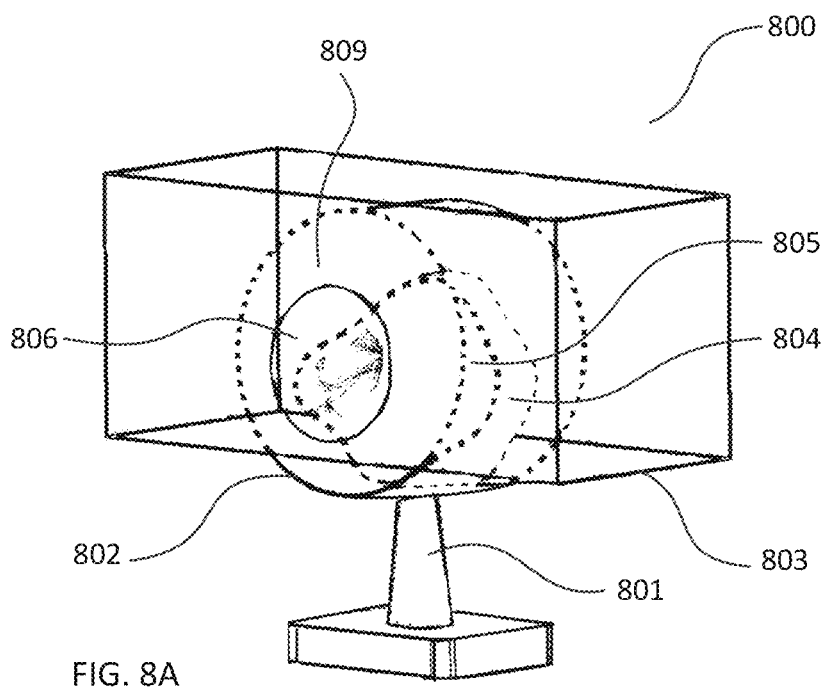
FIGS. 8A-8G. A graphic representation of one embodiment of a machining strategy for making a restoration from a sintered preform.
Figure 8B:
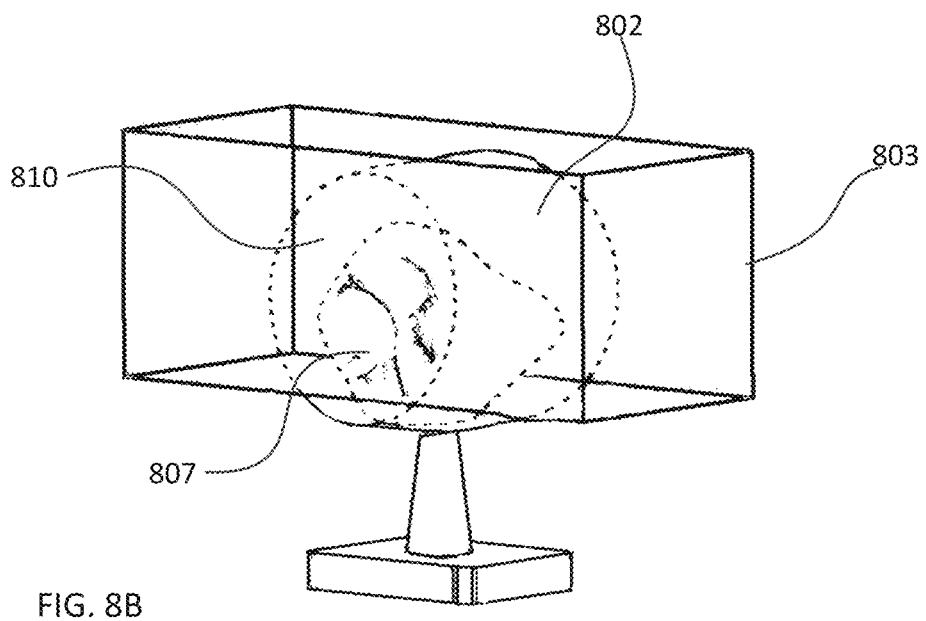
Figure 8C:
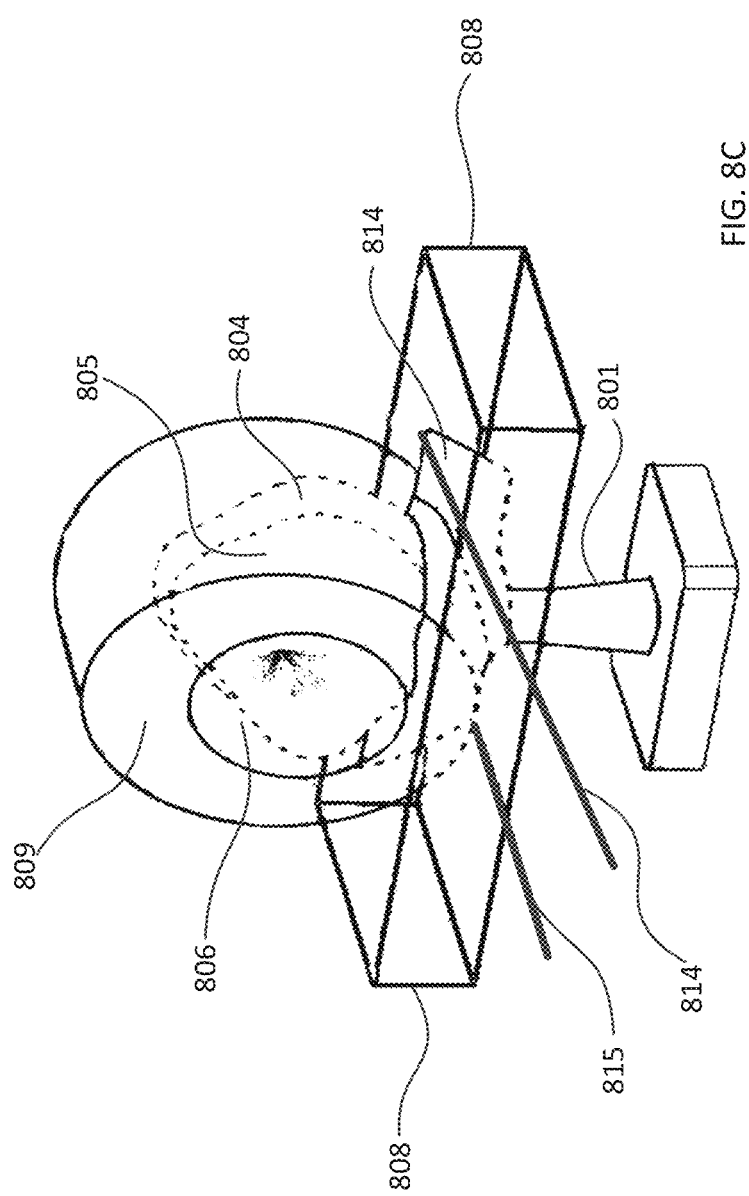

Nesting software may be separate from the dental restoration design software or may comprise a module of the design software which may be automatically implemented upon completion of the restoration design. Nesting information comprising positional data of the stem relative to the dental restoration resulting from the nesting step may be used for computing tools paths. A tool path sequence may be calculated from the positional data of the preform stem and restoration design, which may be split into two or more tool paths. FIGS. 8A, 8B and 8C illustrate a restoration design (804) nested within a model of a preform (802) in which machining steps (800) are split between a front (803) portion and a back (808) portion of the preform body. FIGS. 8A and 8B depict one embodiment of a machining step for a front portion of the preform body (803), corresponding to a portion of the preform body (802) on the side opposite the stem (801); FIG. 8C depicts machining step for machining the back (808) portion of the preform body, which is adjacent the preform stem (801). FIG. 8A illustrates a front portion (803) as seen from the bottom (809) of the preform body (802) having a cavity (806). In FIG. 8A, the inner surface (805) of the restoration design is nested adjacent a preform cavity (806) located on the preform bottom (809). FIG. 8B illustrates a front portion (803) as seen from the top (810) of the preform, and the occlusal surface (807) of the restoration design is adjacent the top (810) of the preform body. FIG. 8C illustrates a machining step for a back (808) portion of a preform body as seen from the preform bottom (809), and the restoration design is nested adjacent the stem (801) of the preform. The front and back portions may each comprise one or more machining steps comprising one or more tool paths to machine a restoration from the preform. In one embodiment, a first tool path is provided for machining the front (803) portion of a preform body and a second tool path is provided for machining the back portion (808) of the preform body adjacent the stem. In one embodiment, a first parallel lacing tool path is provided for machining the front portion and a second parallel lacing tool path is provided for machining the back portion, and the front and back portions are machined from opposite lacing directions relative to the Y-axis.

Figure 8D:
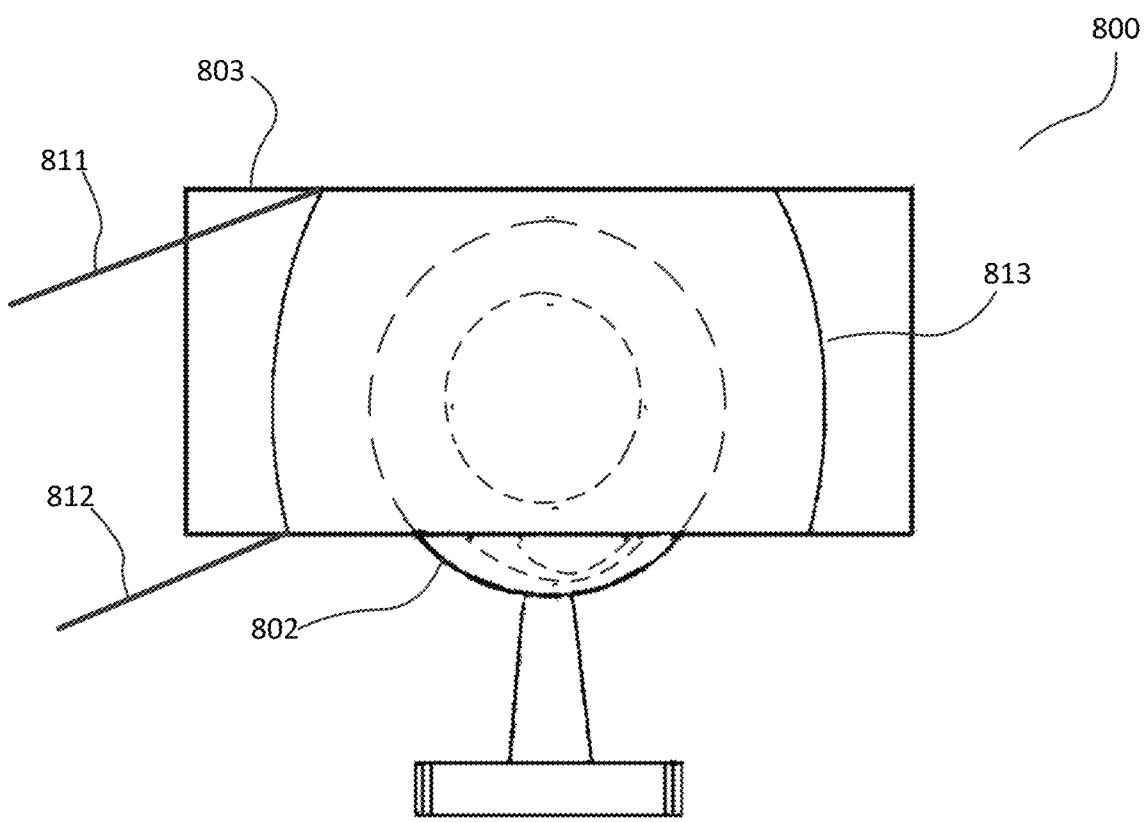
Figure 8E:
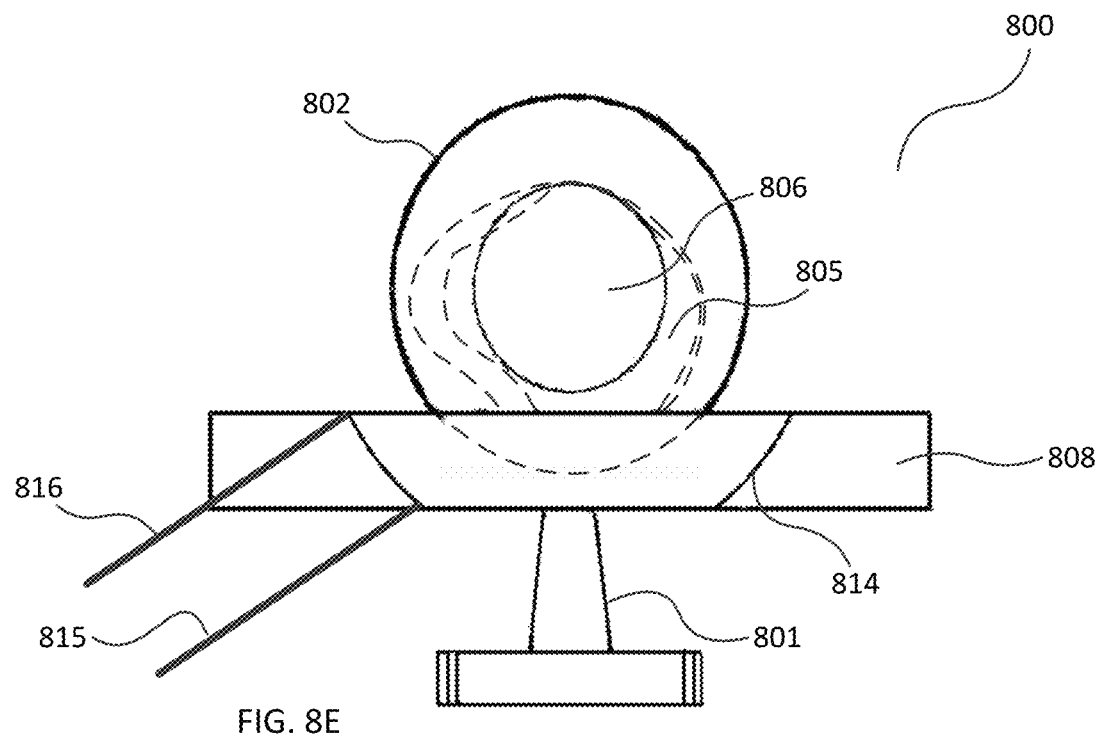
Figure 8F:
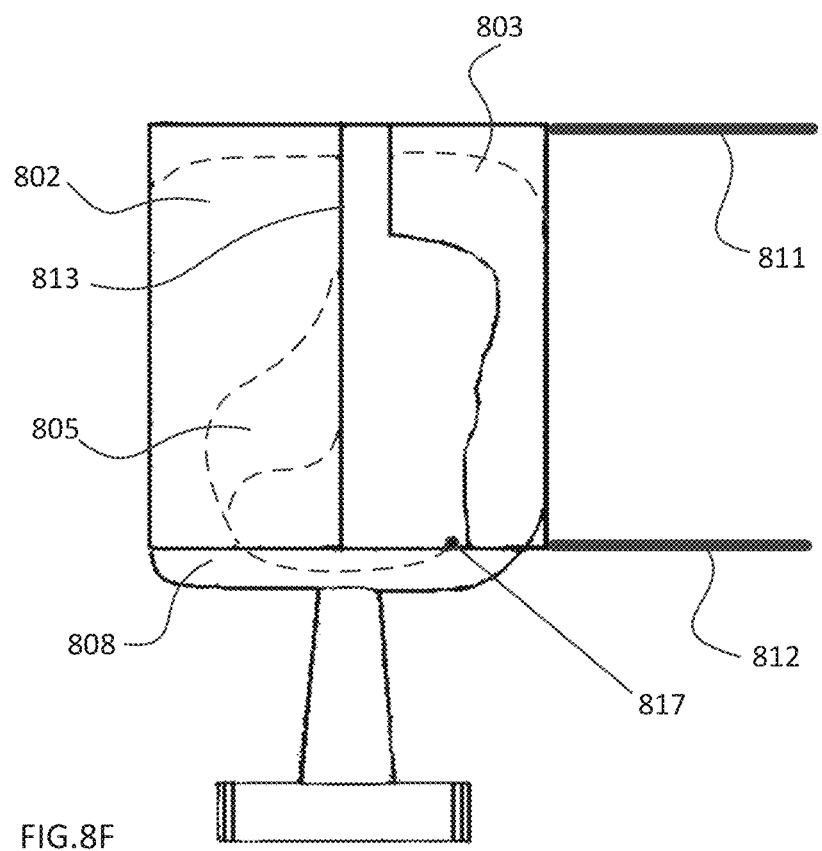
Figure 8G:
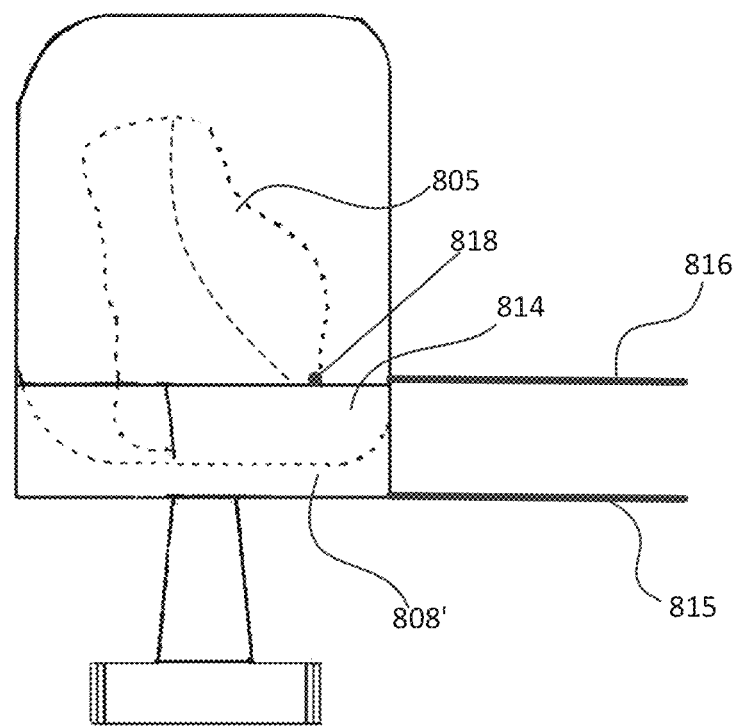

In FIGS. 8C, 8D and 8E, dimensional limits of the milling machine are illustrated by machining steps of front (803) and back (808) portions. Tool offset positions (for example, 813 and 814) may be calculated based on the dimensions of the preform body (802) and stem (801). In one embodiment as exemplified in FIGS. 8F and 8G, two tool paths are provided having front and back tool entry positions (811 and 815, respectively), and front and back tool stop positions (812 and 816, respectively) for front (803) and back (808) portions, as illustrated from a side view of the preform body (802).

In one embodiment, a first machine step comprises a first tool path for machining the back portion (808) of the preform. A first tool path has a back tool entry point (e.g., 815) near the stem (801) side of the preform, and comprises a first parallel lacing tool path in the y-positive direction. A second tool path for machining the front portion has a front tool entry point (e.g., 811) at the front side (803) of the preform, opposite the stem, and comprises a second parallel lacing tool path in Y-negative direction. The first tool path and second tool paths having tool entry points at opposite sides (front and back) of the preform, each follow a lacing pattern that proceed in opposite directions (relative to the Y-axis) toward a point on the y-axis where the tool paths separate. The tool path sequence may be split into first and second tool paths at an arbitrary point relative to the y-axis (e.g., FIGS. 8D and 8E), or the tool path sequence may be split into multiple tool paths based on positional information of the nested restoration, selected to optimize machining parameters described herein. In one embodiment, a tool path sequence for machining the inner (or cavity) surface of the restoration may be separated into the first and second tool paths (with tool path lines generally parallel x-axis direction) at the lowest point (e.g., 712, 818) of the restoration design tooth margin line on the Y-axis that is closest to the preform stem within a set threshold value. The tool path sequence for machining the occlusal surface of the restoration may be separated into first and second tool paths (where tool path lines are generally parallel to the X-axis) at a point (e.g., 110, 711, or 817) relative to the Y-axis in which the edge of the occlusal surface of the restoration design slopes negatively toward the stem at a specified angle.

In an embodiment, a method for shaping a preform body into a dental restoration comprises, at least two tool paths for shaping the top side of a preform body comprising i) a first tool path having a tool path entry at the front end (803) of a preform body (810), and ii) a second tool path having a tool path entry at the back end of a preform body adjacent the stem, and at least two tool paths for shaping the bottom side of a preform body that comprise i) a first tool path having a tool path entry at the front end of a preform top end (810), and ii) a second tool path having a tool path entry at the back end of the preform body adjacent the stem (801).

In one embodiment, a method for shaping a dental restoration design comprises two or more tool paths for shaping the occlusal surface and the inner surface of a restoration design, wherein a tool path for shaping the occlusal surface and a tool path for shaping the inner surface are separated along the restoration parting line that follows the contour or largest dimension of the outer surface of the restoration. In one embodiment, a machining strategy is provided comprising i) a first machining step for machining a first portion of an occlusal side of a restoration design adjacent a stem of a preform body, ii) a second machining step for machining a second portion of an occlusal side of a restoration nested adjacent the front portion of the preform body, iii) a third machining step for machining a first portion of an inner surface side of a restoration design nested adjacent the stem of the preform body, and iv) a forth machining step for machining a second portion of the inner surface side nested near the front portion of the preform body, wherein each step comprises a separate tool path. In one embodiment, the tool enters the first and third tool paths adjacent the stem between the preform body and the attachment, contacting the preform body and removing preform material with a tool side surface, thereby reducing the amount of grinding or material removal by the tool tip. In an embodiment where the preform body comprises a cylindrical form, the tool enters the tool path for the second and fourth tool paths (as described above) adjacent the curved outer surface of the preform on a preform side opposite the stem attachment, wherein the side surface of the grinding tool removes preform material upon entry into the tool path. In one alternate embodiment, either the occlusal surface or the inner surface of a restoration design may be shaped with a single tool path, and the tool path may have an entry point at the front of the preform body or at the back of the preform body adjacent the stem. CAM software may be implemented to generate separate tool paths for front and back portions of the preform body, and the starting and stopping points of the front and back tool paths are determined by identifying a location to separate the tool paths relative to the Y-axis. Front and back tool paths of the restoration design may overlap, for example by about 0.2 mm, to provide blending of the tool path lines at the area in which the tool paths are split. The front and back tool path sequences for the occlusal surface may be split at a location on the Y-axis that is independent of the front and back tool path separation point for the inner surface.

In a further embodiment, a machining step is provided for reducing the dimension of the stem (width or diameter) at the first stem end to facilitate removal of the stem from the shaped restoration design upon completion of the restoration shaping processes described herein. A further tool path may be incorporated into the methods provided herein that has a continuous rotary machining path around the stem length axis, reducing stem width or diameter near the point of contact with the dental restoration.

The order of machining steps and tool paths may vary, and terms such as first and second, for example, as used in first tool path, second tool path, third tool path, first machine step, second machine step, and so forth, are used for descriptive convenience, and should not be connoted as indicative of a specific order of steps unless otherwise noted. An algorithm is provided that comprises parameters that optimize for Z-positive direction positioning of the grinding tool during machining by identifying a nesting position of the restoration design relative to the preform stem as determined based on the methods described herein, and, for an identified nesting position, identifying points on the occlusal and inner side surfaces to split the restoration design into separate tool paths according to the methods disclosed herein.

In a further embodiment, material feed rates may be individually controlled for each machine step. Machining parameters for front and back tool paths may comprise different material feed rates for front and back portions of the preform body. In one embodiment, a first machine step for machining a back portion of the preform body having a tool entry point adjacent the stem comprises a first material feed rate that is faster than the material feed rate of the machining steps for machining the front portion of the preform body when machining the occlusal surface of the restoration design.

Machining parameters may be implemented on a 3+1 axis CNC machine to shape a finished dental restoration from a preform body comprised of material having a Vickers hardness value greater than or equal to about HV4 GPa with a single grinding tool comprising an alloy coating embedded with diamonds in a chair-side application. In another embodiment, the custom dental restoration may be machined in a 3+2, or 4, or 5 axis machine. Corresponding 3+2 or 4 or 5 axis machining cycles may be used to specify a tool axis angle relative to the tool contact normal of the machined surface either directly from the CAD data of the restoration, or indirectly using a separate tool axis drive surface interpolated from the original CAD data. In a further embodiment, more than one grinding tool may be used for grinding the preform. Multiple grinding tools may be used sequentially, for example, for roughing and finishing, or multiple grinding tools may be used simultaneously, on opposite surfaces of the preform.

The methods described herein provide enhanced machining in chairside applications for preform materials having a Vickers hardness value greater than or equal to about HV 4 GPa (Vickers macro-hardness), or a value in the range of HV 4 GPa to HV 20 GPa (i.e., HV 4 GPa to HV 20 GPa), when measured according to the method provided herein. Alternatively, preform materials have a Vickers Hardness value between HV 5 GPa and HV 15 GPa, or between HV 11 GPa and HV 14 GPa. Preform body materials comprising hardness values within this range may include metals, such as cobalt chrome, glass and glass ceramics, such as lithium silicate and lithium disilicate, and ceramic materials, including sintered ceramics comprising alumina and zirconia.

Dental restoration materials, including but not limited to commercially available dental glass, glass ceramic or ceramic, or combinations thereof, may be used for making the preforms that are machinable by the methods described herein. Ceramic materials may comprise zirconia, alumina, yttria, hafnium oxide, tantalum oxide, titanium oxide, niobium oxide and mixtures thereof. Zirconia ceramic materials include materials comprised predominantly of zirconia, including those materials in which zirconia is present in an amount of about 85% to about 100% weight percent of the ceramic material. Zirconia ceramics may comprise zirconia, stabilized zirconia, such as tetragonal, stabilized zirconia, and mixtures thereof. Yttria-stabilized zirconia may comprise about 3 mol % to about 6 mol % yttria-stabilized zirconia, or about 2 mol % to about 7 mol % yttria-stabilized zirconia. Examples of stabilized zirconia suitable for use herein include, but are not limited to, yttria-stabilized zirconia commercially available from (for example, through Tosoh USA, as TZ-3Y grades). Methods form making dental ceramics also suitable for use herein may be found in commonly owned U.S. Pat. No. 8,298,329, which is hereby incorporated herein in its entirety.

The preform body may be made from unsintered materials shaped into an intermediate form having substantially the same geometry as the sintered preform, but with enlarged dimensions to accommodate shrinkage upon sintering, where necessary. Suitable unsintered ceramic materials may be made into blocks by processes including molding and pressing, including biaxial or iso-static pressing, and may optionally comprise binders and processing aids. Ceramic blocks may be shaded so that the sintered preforms have the color of natural or artificial dentition, requiring no further coloring after formation of the dental restoration. Coloring agents may be incorporated during block formation to more closely match the appearance of natural or commercially available artificial dentition than uncolored or unshaded ceramic materials. Optionally, ceramic powder may be processed into blocks by slip casting processes, including processes described in commonly owned U.S. Patent Publication Nos. 2009/0115084; 2013/0231239; and 2013/0313738, incorporated by reference in their entirety. Pre-sintered ceramic blocks suitable for use in making intermediate shaped forms include commercially available ceramic milling blocks including those sold under the trade name BruxZir® (for example, BruxZir® Shaded 16 Milling Blanks, Glidewell Direct, Irvine, Calif.). In some embodiments, the theoretical maximum density of fully sintered zirconia ceramics is between about 5.9 g/cm$^3$ to about 6.1 g/cm$^3$, or for example, or about 6.08 g/cm$^3$ A unitary preform may be shaped from a from a single continuous green-state block or pre-sintered ceramic block, requiring no separate attachment step for attaching the stem and/or attaching member to the preform body. Alternatively, the preform may be made by known molding processes, including injection molding. The intermediate shaped form may be sintered to a density greater than about 95% of the theoretical maximum density by known sintering protocols. Sintered zirconia ceramic preforms may have densities greater than about 95%, or greater than about 98% or greater than about 99%, or greater than about 99.5%, of the maximum theoretical density of the ceramic body.

The preform body comprises materials that are shapeable into dental restorations in chair-side applications by the methods described herein, that have acceptable strength properties for use in anterior, posterior or both anterior and posterior dental restoration applications, without additional post-shaping processing steps to alter the material strength properties after shaping, such as by sintering. Sintered preforms may comprise zirconia ceramic materials that have high flexural strength, including strength values greater than about 400 MPa, or greater than about 500 MPa, or greater than about 600 MPa, or greater than about 800 MPA, when tested by a flexural strength test method for zirconia materials as outlined in ISO 6872:2008, as measured and calculated according to the 3 point flexural strength test described for Dentistry—Ceramic Materials.

Dental restorations may be made by grinding sintered ceramic preforms using grinding tools instead of traditional milling tools because of the material hardness which renders typical milling tools unsuitable in certain embodiments. Grinding tools having a diamond coating, including nickel plated tools embedded with diamonds, are suitable for use herein. A grinding tool (300) having a shank (301), for example as illustrated in FIG. 3, comprises an embedded diamond coating on the shank (301) and tip. Diamonds suitable for use herein include blocky or friable diamonds having an average size in the range of about 90 micron to about 250 micron, or an average size in the range of about 107 micron to about 250 micron, or an average size in the range of about 120 micron to about 250 micron, or for example, an average size in the range of about 120 micron to about 180 micron. Suitable diamond coatings include those in which at least 50% of the diamonds are embedded by a metal alloy layer for more than half the height of the diamond, for example, as determined by SEM analysis. Grinding tools having a coating in which diamonds are embedded in a metal alloy to a depth of about 50% to 95% of the diamond height, or about 60% to about 95% of the diamond height, or to about 80% to about 95% of the diamond height are useful for shaping preforms made from materials such as fully sintered zirconia preforms, or preforms comprising materials having the hardness values described herein. In some embodiments, grinding tools have a diamond coated shank with a metal alloy layer having thickness that is greater than about 50% of the diamond grit size (e.g., in microns), or greater than about 60%, or greater than about 70%, or greater than about 80%, or greater than 90%, or between about 60% and 90%, or between about 80% and 100%, of the diamond grit size (e.g., in microns). In one embodiment, a grinding tool has a diamond coated shank comprising a diamond size in the range of 126 grit to 181 grit, and a nickel alloy layer having a thickness that is greater than or equal to about 70% of the diamond grit size (in microns).

Test Methods

Flexural Strength Test

Flexure tests were performed on sintered test materials using the Instron-Flexural Strength test method for zirconia materials as outlined in ISO 6872:2008.

Test bars were prepared by cutting bisque materials taking into consideration the targeted dimensions of the sintered test bars and the enlargement factor (E.F.) of the material, as follows:

starting thickness=3 mm×E.F.;
starting width=4 mm×E.F.;
starting length=55 mm×E.F.

The cut, bisque bars were sintered substantially according to the sintering profile provided by manufacturer of the bisque material. Flexural strength data was measured and calculated according to the 3 point flexural strength test described in ISO (International Standard) 6872 Dentistry—Ceramic Materials.

Vickers Hardness Number

Preform materials may be tested for hardness using a Vickers hardness (macro-hardness test). Hardness numbers (HV) may be calculated as described in ISO-6507, or by determining the ratio of F/A where F is the force applied in kg/m$^2$ and A is the surface area of the resulting indentation (mm$^2$). HV numbers may be converted to SI units and reported in units, HV GPa, as follows: H(GPa) =0.009817HV.

Examples 1-21

Twenty-one zirconia crowns of multiple tooth types (numbers) were shaped from sintered zirconia preforms by the methods described herein.

Partially sintered zirconia milling blocks were obtained (BruxZir® Shaded milling blocks, Glidewell Direct, Irvine, Calif.) and milled into the shape of a preform by standard milling procedures incorporating an enlargement factor calculated from the block density. The pre-sintered, unitary shaped forms had a cylindrical body, stem and attaching member substantially as depicted in FIGS. 2B-2D, and having a cavity extending inwardly from a bottom surface. The stem had sufficient length between the attaching member and the cylindrical body after sintering for positioning the tip of a ball nose grinding tool in the z-axis direction without contacting the sintered preform. The attaching member shape and size was compatible for attaching to a mandrel used with the CNC machine in the grinding process.

The pre-sintered shaped forms were sintered according to sintering profile of the zirconia blocks provided by the manufacturer to form fully sintered zirconia preforms having a density between about 5.9 g/cm$^3$ and 6.1 g/c m$^3$. The fully sintered preforms had a body length between about 12.8 mm and 14.2 mm, a cross-sectional outer diameter of about 14 mm to 15 mm, a cavity breakout diameter on the bottom end surface having a diameter of about 7 mm to 8 mm; the cavity contour was conical having a depth of about 4 mm. A first stem end had a width of about 2-2.8 and the stem length was between about 6.8 and 7.3 mm.

The preforms each comprised an attachment having a bottom surface glued to metallic mandrels. The preforms were shaped into finished restorations of multiple tooth shapes based on CAD design files using a 3+1 axis CNC machine (TS150™ Chairside mill system, IOS Technologies, San Diego, Calif.) having z-, x-, and y-axes directional movement of grinding tool, plus rotation of the preform between tool path cycles). The grinding tool comprised diamonds (size: about 126 micron) embedded in a nickel alloy plating to an embedded diamond depth of about 80%-90%. A CAM lacing cycle, with step over capability in both planar and the grinding tool axial direction, was utilized to grind all surfaces of the crown. The grinding tool had an average diamond grit size between about 90-210.

An air spindle with rotational speed of about 150000 rpm and a minimum inlet air pressure of about 85 psi were used to grind the fully sintered zirconia preform. The CAM lacing cycle parameters were determined based on tooth number, and grinding surface of the sintered preform relative to the top or bottom of the restoration, the stem side or the side opposite the stem side of the restoration). Restorations were made from the sintered preforms for posterior teeth numbers 2, 3, 14, 15, 18, 19, 30 and 31 in under 60 minutes as seen in Table 1.

TABLE 1

Time to completed restoration from Sintered Preform in Minutes

| Example Number | Tooth # | Time (Minutes) for each Example, respectively |
|---|---|---|
| 1; 2; 3; 4 | 2 | 52; 47; 51; 44 |
| 5; 6; 7; 8 | 3 | 53; 49; 54; 57 |
| 9; 10 | 14 | 47; 51 |
| 11 | 15 | 38 |
| 12; 13; 14 | 18 | 54; 55; 47 |
| 15 | 19 | 49 |
| 16; 17; 18; 19 | 30 | 53; 48; 50; 50 |
| 20; 21 | 31 | 49; 50 |

Figure 1B:
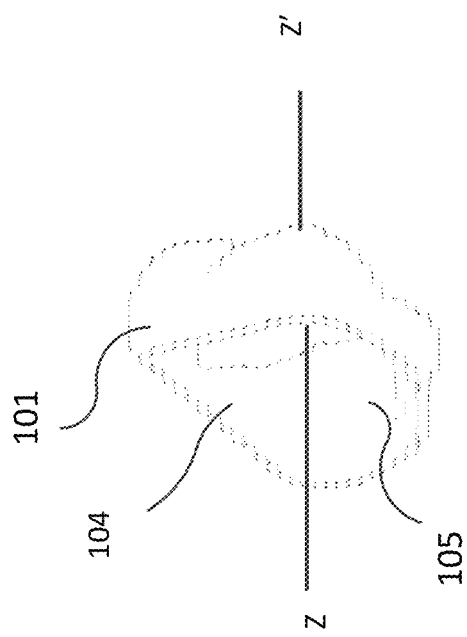
FIG. 1B. A graphic representation of a dental restoration according to one embodiment.
Figure 1C:
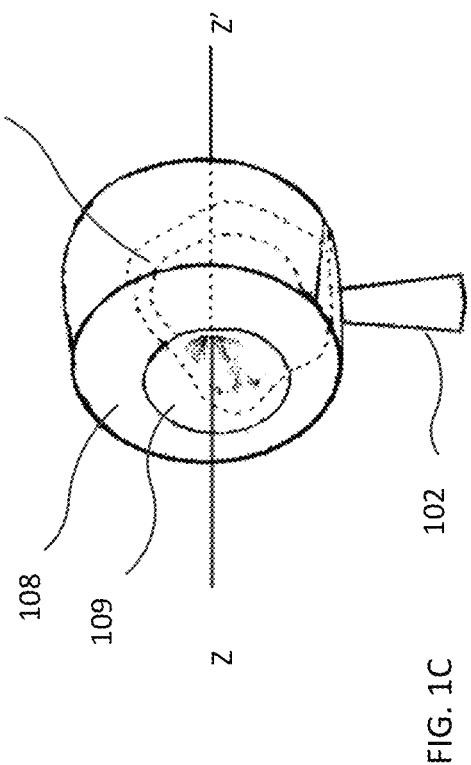
FIG. 1C. A graphic representation of a computer model of a dental restoration nested within a model of the preform.
Figure 1A:
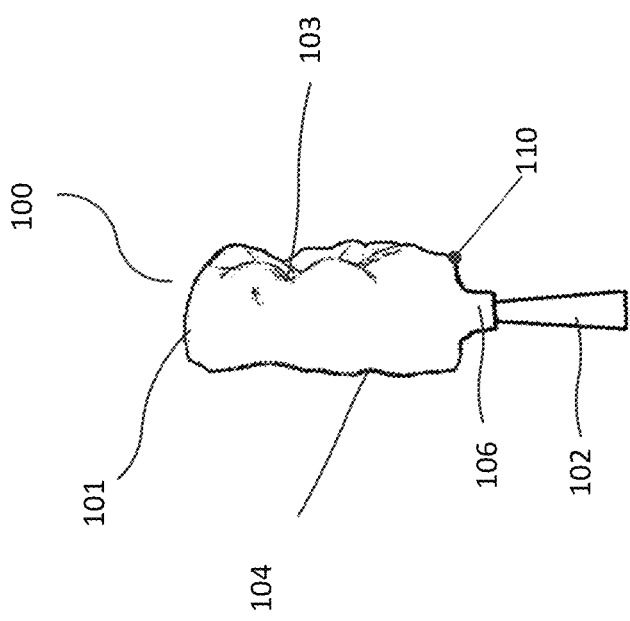
FIG. 1A. A graphic representation of a side perspective view of a dental restoration shaped from a preform and attached to a stem according to one embodiment.

FIG. 1 illustrates a restoration crown made according to the Examples described in Table 1. Restoration crowns were shaped having minimal residual material (106) remaining between the stem and restoration after grinding is completed. The restoration crown was snapped off of the stem, and the location of the stem was hand-sanded to a smooth finish, where necessary.

Examples 22-44

Twenty-two zirconia crowns representing six restoration designs of multiple tooth types (Tooth #2, 14, 15, 30, and 31) were shaped from sintered zirconia preforms that were made substantially according to the methods provided in Examples 1-21.

Restoration designs were generated for multiple tooth preparations corresponding to the following tooth numbers: #2—second molar on upper arch; #14 and #15—first and second molars, respectively, on an upper arch; #30 and #31—first and second molars, respectively, on lower arch using a dental CAD system (IOS™ FASTDESIGN) based on patient scan data. The six custom dental restoration designs were nested within a computer model of a preform to provide placement of the preform stem relative to the tooth design, according to Table 2, with reference to FIGS. 6A and 6B.

Each restoration design was nested four times to provide four nested designs. In each nesting operation, the stem of the preform was positioned in one of four different locations relative to the restoration, as indicated in Table 2. For example, for restoration designs nested with a Number 1 stem position, the Y-axis of the stem was positioned between mesial contact area and buccal surfaces of the restoration design. In the Number 2 stem position, the stem was located between distal contact area and buccal surfaces. In the Number 3 stem position, the stem was located between distal contact area and lingual surface, and in the Number 4 stem position, the stem was located between mesial contact area and lingual surface.

TABLE 2

Machining Time For Shaping Dental Restorations From Sintered Preforms

| Example No. | Tooth # | Stem Position No. | Stem Location | Successful Completion | Time (in minutes) to Completion |
|---|---|---|---|---|---|
| 22 | 31 | 1 | Mesio-buccal | Yes | 49 |
| 23 | | 2 | Disto-buccal | Yes | 53 |
| 24 | | 3 | Disto-lingual | Yes | 50 |
| 25 | | 4 | Mesio-lingual | Yes | 52 |
| 26 | 14 | 1 | Mesio-buccal | Yes | 47 |
| 27 | | 2 | Disto-buccal | Yes | 49 |

TABLE 2-continued

Machining Time For Shaping Dental Restorations From Sintered Preforms

| Example No. | Tooth # | Stem Position No. | Stem Location | Successful Completion | Time (in minutes) to Completion |
|---|---|---|---|---|---|
| 28 |    | 3 | Disto-lingual | Yes | 48 |
| 29 |    | 4 | Mesio-lingual | No | — |
| 30 | 14 | 1 | Mesio-buccal | Yes | 51 |
| 31 |    | 2 | Disto-buccal | Yes | 50 |
| 32 |    | 3 | Disto-lingual | Yes | 54 |
| 33 |    | 4 | Mesio-lingual | No | — |
| 34 | 30 | 1 | Mesio-buccal | Yes | 50 |
| 35 |    | 2 | Disto-buccal | Yes | 52 |
| 36 |    | 3 | Disto-lingual | Yes | 59 |
| 37 |    | 4 | Mesio-lingual | Yes | 59 |
| 38 | 2  | 1 | Disto-buccal | Yes | 54 |
| 39 |    | 2 | Mesio-buccal | Yes | 49 |
| 40 |    | 3 | Mesio-lingual | Yes | 52 |
| 41 |    | 4 | Disto-lingual | No | — |
| 42 | 15 | 1 | Mesio-buccal | Yes | 38 |
| 43 |    | 2 | Disto-buccal | No | — |
| 44 |    | 3 | Disto-lingual | Yes | 42 |
| 45 |    | 4 | Mesio-lingual | No | — |

Positional nesting information was used to calculate four tool path sequences for restoration designs, wherein each restoration design comprised four tool paths. Two tool paths were generated for machining the front portion of the preform and back portion (adjacent the stem) of the preform body for each surface (the occlusal surface and inner surface (cavity side)) of the restoration designs. Restoration designs were machined for each preform using the calculated tool paths.

The results of each example were assessed. Success or failure of shaping a completed restoration is indicated in Table 2, where a lack of success ("No") occurred from tool damage prior to completion of the restoration. The time to shape a restoration from the sintered preform based on nesting conditions was also calculated as seen in Table 2.

All restoration designs in which the tool paths were calculated from nesting operations in which the stem was positioned in a mesio-buccal position were successfully shaped in less than one hour. Eleven out of twelve restoration designs were successfully shaped in under 1 hour from tool paths calculated from nesting positions in which the stems were in a mesio-buccal or disto-buccal position. Three out of 5 restoration designs in which the tool paths were calculated based on positional data in which the stem was nested in the mesio-lingual position were unsuccessfully shaped. The shortest shaping time to shape all successful restorations occurred for tool paths calculated from nesting positions in which the stem location was buccally oriented (a mesio-buccal or disto-buccal position).

We claim:

1. A computer-implemented method for generating machining instructions to make a final dental restoration suitable for placement in a patient's mouth from a preform body comprised of a sintered ceramic material, comprising:
   a. obtaining i) a computerized design of a posterior dental restoration crown for a patient and ii) a computer model of a sintered ceramic preform body; and
   b. generating machining instructions for shaping the sintered ceramic perform body into a final, posterior dental restoration crown with a single grinding tool in less than 1 hour,
   wherein the grinding tool comprises a diamond coating on a tool shank, and
   wherein the diamond coating comprises diamonds that are embedded in a metal alloy layer to a depth that is between 60% to 95% of a diamond height (in microns).

2. The computer-implemented method of claim 1, wherein the diamond coating comprises an average diamond size in the range of 90 μm to 250 μm.

3. The computer-implemented method of claim 1, wherein the diamonds are embedded in the metal alloy layer to a depth that is between 80% and 95% of the diamond height (in microns).

4. The computer-implemented method of claim 1, wherein the preform body is comprised of a sintered ceramic zirconia material having greater than 95% theoretical density.

5. The computer-implemented method of claim 1, wherein the metal alloy comprises nickel.

6. The computer-implemented method of claim 1, wherein the machining instructions comprise a lacing tool path having sequential tool path lines, and the method further comprises inserting an additional tool path line between two sequential tool path lines if a Z increment value between the two sequential tool path lines in a Z– negative direction is greater than a threshold value.

7. A computer-implemented method for generating machining instructions to make a dental restoration from a preform body that comprises a fully sintered zirconia material, comprising:
   a. obtaining i) a computerized design of a dental restoration for a patient and ii) a computer model of a preform body; and
   b. generating machining instructions for shaping the dental restoration from the preform body that comprises the sintered zirconia material with a grinding tool that comprises a diamond coating,
   wherein the diamond coating comprises diamonds that are embedded in a metal alloy layer, and the metal alloy layer has a thickness that is greater than 60% of a diamond grit size (in microns) of the diamonds.

8. The computer-implemented method of claim 7, wherein the diamond coating comprises a diamond grit size (in microns) that is in the range of 90 to 250.

9. The computer-implemented method of claim 7, wherein the metal alloy layer has a thickness between 60% and 90% of the diamond grit size (in microns).

10. The computer-implemented method of claim 7, wherein the metal alloy layer has a thickness between 80% and 100% of the diamond grit size (in microns).

11. The computer-implemented method of claim 7, wherein the machining instructions comprise a lacing tool path pattern having sequential tool path lines, and the method further comprises inserting an additional tool path line between two sequential tool path lines if a threshold value for machining in a Z-negative direction is exceeded.

12. The computer-implemented method of claim 11, wherein the threshold value for machining in the Z-negative direction is less than 10% of the diamond grit size (in microns).

13. The computer-implemented method of claim 7, wherein the machining instructions comprise limiting an amount of continuous machining in a Z– negative direction.

14. A computer-implemented method for generating machining instructions to make a dental restoration from a preform body comprising:
   a. obtaining i) a computerized design of a dental restoration of a patient and ii) a computer model of a preform body;

b. generating machining instructions comprising at least one machining step for shaping the dental restoration from the preform body with a grinding tool,
wherein the grinding tool comprises a diamond coating comprising diamonds embedded in a metal alloy layer, and
wherein the at least one machining step comprises a tool path comprising sequential tool path lines; and
c. inserting an additional tool path line between the two sequential tool path lines if a Z increment value between sequential tool path lines is greater than a threshold value for machining in a Z-negative direction,
wherein the threshold value for machining in the Z-negative direction is less than or equal to 10% of a diamond grit size (in microns) of diamonds of the diamond coating.

15. The computer-implemented method of claim 14, wherein the diamond grit size (in microns) is in the range of 90 to 210.

16. The computer-implemented method of claim 14, wherein the diamond coating is on a shank of the grinding tool.

17. The computer-implemented method of claim 14, wherein the diamond coating comprises diamonds embedded in a metal alloy layer, and the metal alloy layer comprises a thickness between 60% and 90% of the diamond grit size (in microns).

18. The computer-implemented method of claim 14, wherein a step-over distance in a Y-direction between the two sequential tool path lines is decreased to insert the additional tool path line.

19. The computer-implemented method of claim 14, wherein the machining instructions comprise at least one machining step for shaping a back portion of the preform body and at least one machining step for shaping a front portion of the preform body.

20. The computer-implemented method of claim 14, wherein the method comprises machining instructions for shaping a finished dental restoration crown from a sintered ceramic preform body using a single grinding tool in less than 1 hour.

* * * * *